(12) United States Patent
Cardin

(10) Patent No.: US 7,875,596 B2
(45) Date of Patent: Jan. 25, 2011

(54) USE OF DERMATAN SULFATES AND/OR DESULFATED HEPARINS TO TREAT OR PREVENT HEPARINOID-INDUCED AUTOIMMUNE RESPONSES

(75) Inventor: Alan D. Cardin, Cincinnati, OH (US)

(73) Assignee: Celsus Biopharmaceuticals, Inc., Cincinnati, OH (US)

( * ) Notice: Subject to any disclaimer, the term of this patent is extended or adjusted under 35 U.S.C. 154(b) by 437 days.

(21) Appl. No.: 12/014,948

(22) Filed: Jan. 16, 2008

(65) Prior Publication Data

US 2008/0138380 A1 Jun. 12, 2008

Related U.S. Application Data

(62) Division of application No. 11/132,317, filed on May 19, 2005, now abandoned.

(60) Provisional application No. 60/572,364, filed on May 19, 2004.

(51) Int. Cl.
*A61K 31/737* (2006.01)
*C08B 37/08* (2006.01)
*C08B 37/10* (2006.01)
*A61K 31/727* (2006.01)

(52) U.S. Cl. .................. 514/56; 514/54; 536/55.1; 536/123; 536/123.1

(58) Field of Classification Search ............... None
See application file for complete search history.

(56) References Cited

U.S. PATENT DOCUMENTS

| | | | |
|---|---|---|---|
| 4,373,023 A | 2/1983 | Langer et al. | |
| 4,757,057 A | 7/1988 | Fussi et al. | |
| 4,943,630 A | 7/1990 | Jacquinet | |
| 4,987,222 A | 1/1991 | De Ambrosi et al. | |
| 5,100,383 A * | 3/1992 | Lichtenstein | 604/98.01 |
| 5,262,325 A | 11/1993 | Zimmermann et al. | |
| 5,296,471 A | 3/1994 | Holme et al. | |
| 5,389,618 A | 2/1995 | Debrie | |
| 5,466,582 A | 11/1995 | Amiral | |
| 5,567,417 A | 10/1996 | Sasisekharan et al. | |
| 5,650,386 A | 7/1997 | Leone-Bay et al. | |
| 5,668,118 A | 9/1997 | Kennedy | |
| 5,707,974 A | 1/1998 | Kennedy | |
| 5,808,021 A | 9/1998 | Holme et al. | |
| 5,912,237 A | 6/1999 | Kennedy | |
| 5,922,690 A | 7/1999 | Van Gorp et al. | |
| 5,965,121 A | 10/1999 | Leone-Bay et al. | |
| 5,972,717 A | 10/1999 | Aster et al. | |
| 5,972,718 A | 10/1999 | Moghaddam et al. | |
| 5,990,097 A | 11/1999 | Kennedy | |
| 5,995,208 A * | 11/1999 | Sarge et al. | 356/39 |
| 6,077,683 A | 6/2000 | Kennedy | |
| 6,093,563 A | 7/2000 | Bennett et al. | |
| 6,486,137 B1 | 11/2002 | Lundquist et al. | |
| 6,518,244 B2 | 2/2003 | Cardin et al. | |
| 6,579,725 B1 | 6/2003 | Seeberger et al. | |
| 6,846,917 B2 | 1/2005 | Seeberger et al. | |
| 7,279,177 B2 * | 10/2007 | Looney et al. | 424/443 |
| 7,468,358 B2 | 12/2008 | Kennedy et al. | |
| 2003/0092671 A1 | 5/2003 | Johansen et al. | |
| 2007/0123489 A1 | 5/2007 | Kennedy et al. | |

FOREIGN PATENT DOCUMENTS

| | | |
|---|---|---|
| EP | 0040144 | 11/1986 |
| WO | WO 93/05075 | 3/1993 |
| WO | WO 94/09034 | 4/1994 |
| WO | WO 98/55514 | 12/1998 |
| WO | WO 99/38827 | 8/1999 |
| WO | WO 02-20091 | 3/2002 |

OTHER PUBLICATIONS

Silverman, "The Organic Chemistry of Drug Design and Drug Action" Published 1992 by Academic Press, chapter 2, pp. 4-47.*
Taliani et al., "Dermatan Sulfate in Patients with Heparin-induced Thrombocytopenia" British Journal of Haematology (1999) vol. 104, pp. 87-89.*
Tcheng, "Clinical Challenges of Platelet Blycoprotein IIb/IIIa Receptor Inhibitor Therapy: Bleeding, Reversal, Thrombocytopenia, and Retreatment," *Am. Heart J.* (2000) 139(2):538-45.
Tollefsen et al., "Modulation of Heparin Cofactor II Activity by Histidine-Rich Glycoprotein and Platelet Factor 4," *J. Clin Invest.* (1985) 75:496-501.
Trossaert et al., "High Incidence of Anti-Heparin/Platelet Factor 4 Antibodies After Cardiopulmonary Bypass surgery," *Br. J. Haematol.* (1998) 101(4):653-55.
Utley, "Cardiopulmonary Bypass Surgery," *Curr. Opin. Cardiol.* (1992) 7(2):267-75.
Vahdat et al, "Fatal Cerebral Hemorrhage and Severe Thrombocytopenia During Abciximab Treatment," *Cath. Cardio. Interv.* (2000) 49:177-80.
Van Demem et al., "Determinations of the Molecular Mass of Low Molecular Mass (LMM) Heparin," *Pharmeuropa* (1991) 3:202-25.
Visentin et al., "Antibodies from Patients with Heparin-Induced Thrombocytopenia/Thrombosis Are Specific for Platelet Factor 4 Complexed with Heparin or Bound to Endothelial Cells," *J. Clin. Invest.* (1994) 93:81-88.

(Continued)

*Primary Examiner*—Eric S Olson
(74) *Attorney, Agent, or Firm*—Eric W. Guttag; Eric W. Guttag IP Law Office

(57) ABSTRACT

Dermatan sulfates and/or O-desulfated heparins useful in treating and preventing heparinoid-induced autoimmune responses, in particular heparin-induced thrombocytopenia (HIT) and its associated disease states. The dermatan sulfates comprise repeating disulfated and/or trisulfated disaccharide units of L-iduronic acid and N-acetyl-D-galactosamine. The O-desulfated heparins comprise heparin molecules selectively O-desulfated at the 2-O and/or 3-O positions of the uronic acid and glucosamine saccharide residues. Particularly effective dermatan sulfate HIT antagonists have a mean molecular weight of from about 2000 to about 10,000 Daltons.

19 Claims, 7 Drawing Sheets

OTHER PUBLICATIONS

Visentin et al., "Heparin Is not Required for Detection of Antibodies Associated with Heparin-Induced Thrombocytopenia/Thrombosis," *J. Lab. Clin. Med.* (2001) 138:22-31.

Walenga et al., "Clinical Experience with Combined Treatment of Thrombin Inhibitors and GPIIb/IIIa Inhibitors in Patients with HIT," *Semin. Thromb. Hemost.* (1999) 25(Suppl I): 77-81.

Walenga et al., "Intimatan Ameliorates the Activation of Human Platelets by Heparin/Heparin Antibody from Patients with Heparin-Induced Thrombocytopenia," Slide of Loyola University Medical Center and Celsus Laboratories, Inc.

Walenga et al., "Combined Thrombin and Platelet Inhibition Treatment for HIT Patients," *Hämostaseologie* (1999) 19:128-33.

Walenga et al., "Laboratory Tests for the Diagnosis of Heparin-Induced Thrombocytopenia," *Semin. Thromb. Hemost.* (1999) 25 (Suppl 1): 43-49.

Wallis et al., "Failure of Early Heparin Cessation as Treatment for Heparin-Induced Thrombocytopenia," *Am. J. Med.* (1999) 106(6): 629-635.

Warkentin et al, "Temporal Aspects of Heparin-Induced Thrombocytopenia," *N. Eng. J. Med.* (2001) 344:1286-1292.

Warkentin et al., "A 14-Year Study of Heparin-Induced Thrombocytopenia," *Am. J. Med.* (1996) 101:502-507.

Xuchong et al., "Generation of Anti-Hirudin Antibodies in Heparin-Induced Thrombocytopenic Patients Treated with R-Hirudin," Circulation (1999) 1528-32.

Yang et al., "Intimatan, A Heparin Cofactor II Catalyst, Inhibits Vessel Wall Thrombogenicity and Intimal Hyperplasia More Effectively than Heparin," 1311:414.

Zhasng et al., "Crystal Structure of Recombinant Hum Platelet Factor 4," *Biocemistry* (1994) 33:8361-66.

Merriam-Webster's Collegiate Dictionary, Tenth Edition, published 1998 by Merriam-Webster, Incorporated, p. 924.

Van Dedem, et al. "Determinations of the Molecular Mass of Low Molecular Mass (LMM) Heparin" *Pharmaeuropa*, vol. 3, No. 3, (Oct. 1991), pp. 202-218.

Taube, et al., "Inhibition of Complement Activation Decreases Airway Inflammation and Hyperresponsiveness" American Journal of Respiratory and Critical Care Medicine (2003), vol. 168, pp. 1333-1341.

Blain, et al., "Expression System for High Levels of GAG Lyase Gene Expression and Study of the heap Upstream Region in *Flavobacterium heparinum*" Journal of Bacteriology (2002), vol. 184, pp. 3242-3252/.

Bar-Shavit et al., "Binding of Thrombin to Subendothelial Extracellular Matrix," *J. Clin Invest.* (1989) 84:1096-1104.

Bauer et al., "Prevalence of Heparin-Associated Antibodies without Thrombosis in Patients Undergoing Cardiopulmonary Bypass Surgery," *Circulation* (1997)95:1242-46.

Blank et al., "Anti-Platelet Factor 4/Heparin Antibodies from Patients with Heparin-Induced Thrombocytopenia Provoke Direct Activation of Microvascular Endothelial Cells," *Int. Immunol.* (2002) 14:121-29.

Bock et al., "The Multiple Complexes Formed by the Interaction of Platelet Factor 4 with Heparin," *Biochem. J.* (1980) 191:709-10.

Brandjes et al., "Acenocoumarol and Heparin Compared with Acenocoumarol Alone in the Initial Treatment of Proximal-Vein Thrombosis," *N. Engl. J. Med.* (1992) 327(21): 1485-89.

Brieger et al., "Heparin-Induced Thrombocytopenia," *J. Am. Coll. Cardiol.* (1998) 31:1449-1459.

Charles et al., "The Three Dimensional structure of Bovine Platelet Factor 4 at 3.0 Å Resolution,"*J. Biol. Chem*. (1989) 264:2092-99.

Fahey, "Heparin-Induced Thrombocytopenia." *J. Vasc. Nurs*. (1995) 13:112-116; http://www.argatroban.com/ref 0.1 htm, 2004.

Goad et al., "Pentosan-Induced Thrombocytopenia: Support for an Immune Complex Mechanism," *Brit. J. Haematol.* (1994) 88:803-08.

Greinacher et al., "Characterization of the Structural Requirements for a Carbohydrate Based Anticoagulant with a Reduced Risk of Inducing the Immunological Type of Heparin-Associated Thrombocytopenia," *Thromb. Haemost.* (1995) 74:886-892.

Greinacher et al., "Heparin-Associated Thrombocytopenia in a Patient Treated with Polysulphated Chondroitin Sulphate: Evidence for Immunological Crossreactivity between Heparin and Polysulphated Glycosaminoglycan," *Brit. J. Haematol.* (1992) 81: 252-54.

Greinacher et al., "Heparin-Associated Thrombocytopenia: Isolation of the Antibody and Characterization of a Multimolecular PF4-Heparin Complex as Major Antigen," *Thromb. Haemost.* (1994) 71:247-51.

Greinacher et al., "Heparin-Associated Thrombocytopenia: the Antibody Is Not Heparin Specific," *Thromb. Haemost.* (1992) 67: 545-549.

Greinacher et al., "Lepirudin (Recombinant Hirudin) for Parenteral Anticoagulation in Patients with Heparin-Induced Thrombocytopenia," *Circulation* (1999):587-93.

Greinacher, "Treatement Options for Heparin-Induced Thrombocytopenia," *Am. J. Helath-Syst. Pharm.* (2003) 60(20:S12-S18; http://www.medscape.com/viewarticle/463457.

Jappe et al., "Allergy to Heparin, Heparinoids, and Recombinant Hirudin: Diagnostic and Therapeutic Alternatives," *Hartarzt* (1999) 50(6): 406-11.

Kawapisz et al., "Prolonged Bleeding after Cardiopulmonary Bypass with Recombinant Hirudin in Heart Transplantation," *Eur. J. Cardiothroac. Surg.* (1999) 16(2): 256-57.

King et al., "Heparin-Associated Thrombocytopenia," *Ann. Intern. Med.* (1984) 100:535-40.

Kiss, "β-Eliminative Degradation of Carbohydrates Containing Uronic Acid Residues," *Adv. Carbohydr. Chem. Biochem.*, (1974) 29:229-303.

Kodityal et al., "Danaparoid for Heparin-Induced Thrombocytopenia: An Analysis of Treatment Failures," *Eur. J. Haematol.* (2003) 71:109-13.

Lane et al., "Anticoagulant Activities of Heparin Oligosaccharides and their Neutralization by Platelet Factor 4," *Biochem J.* (1984) 218:725-32.

Kikura, et al., "Heparin Neutralization with Methylene Blue, Hexadimethrine, or Vancomycin After Cardiopulmonary Bypass," Anest. Analg. 1996; 83:233-7.

Lee et al. "Anti-Heparin Platelet Factor 4 Antibody Is a Risk Factor for Vascular Access Obstruction in Patients Undergoining Hemodialysis," *J. Korean Med. Sci.* (2003) 18:69-72.

Li et al., "Defining a Second Epitope for Heparin-Induced Thrombocytopenia/Thrombosis Antibodies Using KKO, a Murine HIT-like Monoclonal Antibody," *Blood* (2002) 99:1230-36.

Liberti et al., "Physiochemical Studies of Fractionated Bovine Heparin II: Viscosity as a Function of Ionic Strength,"*Arch. Biochem. Biophys.* (1967) 119:510-18.

Mascellani et al., "Relative Influence of Different Disulphate Disaccharide Clusters on the HCII-Mediated Inhibition of Thrombin by Dermatan Sulphates of Different Origins," *Thrombosis Res.* (1994) 74:605-15.

Mousa et al., "Intranasal Antiplatelet/Antithrombotic Efficacy of a Novel Platelet GPIIB/IIIA Receptor Antagonist DMP755," *Thromb. Res.* (1998) 92:115-124.

Mulloy et al., "Molecular Weight Measurements of Low Molecular Weight Heparins by Gel Permeation Chromatography," *Thrombosis Haemostasis* (1997) 77(4):668:74.

Nicolini et al., "Combination of Platelet Fibrinogen Receptor Antagonist and Direct Thrombin Inhibitor at Low Doses Markedly Improves Thrombolysis," Circulation (1994) 89(4): 1802-9.

Nunnohamed et al., "Clinical Experience with a New Antithrombotic (Dermatan Sulfate) in Chronic Hemodialysis Patients," *Clin. Nephrology* (1993) 39(3):166-71.

Okwusidi et al., "Fibrin Moderates the Catalytic Action of Heparin but not that of Dermatan Sulfate on Thrombin Inhibition in Human Plasma," *J. Lab Clin. Med.* (May 1991) 117:359-64.

Pavão et al., "Highly Sulfated Dermatan Sulfates from Ascidians: Structure versus Anticoagulant Activity of these Glycosaminoglycans," *J. Biol. Chem.* (1998) 273:27848-57.

Petersen et al., "Characterization of a Neutrophil Cell Surface Glycosaminoglycan that Mediates Binding of Platelet Factor 4," *J. Biol. Chem.* (1999) 274: 12376-82.

Pouplard et al., "Antibodies to Platelet Factor 4-Heparin After Cardiopulmonary Bypass in Patients Anticoagulated with Unfractionated Heparin or a Low Molecular Weight Heparin: Clinical Implications for Heparin-Induced Thrombocytopenia," *Circulated* (1999) 99:2536-39.

Pouplard et al., "Induction of Monocyte Tissue Factor Expression by Antibodies to Heparin-Platelet Factor 4 Complexes Developed in Heparin-Induced Thrombocytopenia," *Blood* (2001) 97:3300-302.

Rao et al., "Glycoprotein IIb/IIIa Receptor Antagonist Tirofiban Inhibits Thrombin Generation during Cardipplumonary Bypass in Baboons," *Thromb. Haemost.* (1999) 82(1): 140-44.

Scully et al., "Effect of Oversulphated Chondroitin and Dermatan Sulfate upon Thrombin and Factor Xa Inactivation by Antithrombin III," *Biochem. J.* (1988) 254:547-51.

Shaklee et al., "The Disaccharides Formed by Deaminative Cleavage of N-Deacetylated Glycosaminoglycans," *Biochem J.* (1986) 235:225-36.

Silver et al., "Heparin-Induced Thrombocytopenia, Thrombosis, and Hemorrhage," *Ann. Surg.* (1983) 198:301-306.

Stuckey et al., "A Model of Platelet Factor 4 Complex with Heparin," *Proteins: Structure, Function and Genetics* (1992) 14:277-87.

Suh et al., "Antibodies from Patients with Heparin-Induced Thrombocytopenia/Thrombosis Recognize Different Epitopes on Heparin:Platelet Factor 4," *Blood* (1998) 91:916-22.

Talinai et al., "Dermatan Sulphate in Patients with Heparin-Induced Thrombocytopenia," *Br. J. Haematol.* (1999) 104:87-89.

* cited by examiner

USE OF DERMATAN SULFATES AND/OR DESULFATED HEPARINS TO TREAT OR PREVENT HEPARINOID-INDUCED AUTOIMMUNE RESPONSES

CROSS-REFERENCE TO RELATED APPLICATIONS

This application is a divisional of U.S. application Ser. No. 11/132,317 filed May 19, 2005 now abandoned, which claims the benefit of U.S. Provisional Application No. 60/572,364 filed May 19, 2004. The entire disclosure and contents of the above applications are hereby incorporated by reference.

GOVERNMENT INTEREST STATEMENT

This invention was made in part with Government support under Grant No. HL-66-646-01 and HL-70-453-01 awarded by the National Institute of Health, National Heart, Lung & Blood Institute. The Government may have certain rights to the invention.

BACKGROUND

1. Field of the Invention

The present invention relates to treating and/or preventing heparinoid-induced autoimmune responses with certain dermatan sulfates and/or certain O-desulfated heparins. The present application particularly relates to the treatment and/or prevention of heparin-induced thrombocytopenia (HIT) and its associated disease states with certain dermatan sulfate and/or certain O-desulfated heparin HIT antagonists.

2. Related Art

Heparin and related heparinoids are sulfated mucopolysaccharides that belong to the family of glycosaminoglycans (GAGs). Over one trillion units of heparin are administered to 12 million patients annually in the United States for the prevention and treatment of thrombo-embolic diseases. See Fahey, "Heparin-Induced Thrombocytopenia." *J. Vasc. Nurs.* (1995) 13:112-116; http://www.argatroban.com/ref 01htm, 2004. Cardiovascular-related thrombo-embolic diseases are among the leading causes of death in the United States. With perhaps the exception of stroke, the most widely prescribed anticoagulant for the prevention and treatment of these diseases is heparin. Heparin is ubiquitous throughout hospitals and is used routinely to keep all intravenous and other access lines to the patient from clotting.

While bleeding is a well understood side-effect of heparin, its use is also associated with a drug-induced, autoimmune hypersensitivity response that, paradoxically, predisposes the patient to develop severe thrombocytopenia and thrombosis, and is typically referred to as heparin-induced thrombocytopenia (HIT). The cardiology patient (e.g., a patient undergoing cardiopulmonary bypass surgery) is particularly predisposed to HIT because multiple exposures to heparin can occur prior to surgery that sensitize the patient to the high doses of heparin required to suppress the massive hypercoagulation response to surgery. See Bauer et al., "Prevalence of Heparin-Associated Antibodies without Thrombosis in Patients Undergoing Cardiopulmonary Bypass Surgery," *Circulation* (1997) 95:1242-46; Pouplard et al., "Antibodies to Platelet Factor 4-Heparin After Cardiopulmonary Bypass in Patients Anticoagulated with Unfractionated Heparin or a Low Molecular Weight Heparin: Clinical Implications for Heparin-Induced Thrombocytopenia," *Circulation* (1999) 99:2536-39; Trossaert et al., "High Incidence of Anti-Heparin/Platelet Factor 4 Antibodies After Cardiopulmonary Bypass surgery," *Br. J. Haematol.* (1998) 101(4):653-55; Utley, "Cardiopulmonary Bypass Surgery," *Curr. Opin. Cardiol.* (1992) 7(2):267-75.

Approximately 2-5% of all patients in the U.S. exposed to heparin develop an antibody-mediated hypersensitivity to heparin with associated thrombocytopenia, referred to as Type II HIT, with a significantly greater percentage developing antibodies without thrombocytopenia. See Wallis et al., "Failure of Early Heparin Cessation as Treatment for Heparin-Induced Thrombocytopenia," *Am. J. Med.* (1999) 106 (6): 629-635; Warkentin et al., "A 14-Year Study of Heparin-Induced Thrombocytopenia," *Am. J. Med.* (1996) 101:502-507; Brieger et al., "Heparin-Induced Thrombocytopenia," *J. Am. Coll. Cardiol.* (1998) 31:1449-1459. HIT disease can range from clinically insignificant to extremely severe. In contrast to the hemorrhagic thrombocytopenia disease states, HIT is associated with an increased risk of thrombosis. Historically, about 40% of these HIT patients develop a life-threatening thrombosis or HITT syndrome that produces devastating complications including necrosis of the extremities, stroke, myocardial infarction and pulmonary embolism. See Pouplard et al, supra; Trossaert et al, supra. Morbidity rates among HIT patients can reach as high as 61%, including a limb amputation rate of approximately 20% and an overall mortality rate of approximately 30%. See Silver et al., "Heparin-Induced Thrombocytopenia, Thrombosis, and Hemorrhage," *Ann. Surg.* (1983) 198: 301-306; King et al., "Heparin-Associated Thrombocytopenia," *Ann. Intern. Med.* (1984) 100:535-40; Utley, supra; Wallis et al., supra.

HIT can occur relatively rapidly after exposure to heparin. In a recent study, the onset of HIT occurred on or after day 4 of heparin therapy in 70% of patients; an even more rapid onset of HIT occurred in 30% of these patients, i.e., after 10.5 hours of heparin exposure. See Warkentin et al, "Temporal Aspects of Heparin-Induced Thrombocytopenia," *N. Eng. J. Med.* (2001) 344: 1286-1292. Diagnosis is often based on a decline in platelet numbers and the exclusion of other causes of thrombocytopenia.

The prothrombotic state of HIT is caused in part by an immunologic reaction to heparin exposure that promotes platelet activation antecedent to thrombocytopenia and thrombosis. The immunological response to heparin exposure may also damage the endothelial cells that form the vascular lining and induce Tissue Factor expression in monocytes, thereby further enhancing the procoagulant state. See Visentin et al., "Antibodies from Patients with Heparin-Induced Thrombocytopenia/Thrombosis Are Specific for Platelet Factor 4 Complexed with Heparin or Bound to Endothelial Cells," *J. Clin. Invest.* (1994) 93:81-88; Blank et al., "Anti-Platelet Factor 4/Heparin Antibodies from Patients with Heparin-Induced Thrombocytopenia Provoke Direct Activation of Microvascular Endothelial Cells," *Int. Immunol.* (2002) 14:121-29; Pouplard et al., "Induction of Monocyte Tissue Factor Expression by Antibodies to Heparin-Platelet Factor 4 Complexes Developed in Heparin-Induced Thrombocytopenia," *Blood* (2001) 97:3300-302.

Platelet activation is caused by an interaction of the heparinoid-induced immune complexes with the FcγIIa receptor on the cell surface. The major factors eliciting platelet activation with sera of HIT type II patients have previously been attributed to the degree of sulfation and molecular weight of the GAG, and not the type of glycosidic linkage of the oligosaccharide or the antithrombin III binding capacity of the GAG. Branched glucan sulfates form immune complexes with patient sera and activate platelets at lower concentrations than linear glucan sulfates. The suggested optimal size GAG for HIT antigen formation, immune complex formation and subsequent platelet activation is a hexadecasaccharide of 4800 Daltons. See Greinacher et al., "Heparin-Associated Thrombocytopenia: the Antibody Is Not Heparin Specific," *Thromb. Haemost.* (1992) 67: 545-549; Greinacher et al., "Characterization of the Structural Requirements for a Carbohydrate Based Anticoagulant with a Reduced Risk of Inducing the Immunological Type of Heparin-Associated Thrombocytopenia," *Thromb. Haemost.* (1995) 74: 886-892. Thus, it has been previously concluded that hyper- or oversulfation of GAGs is an inappropriate approach to anticoagulation based on the HIT inducing potential of sulfated GAGs, and that to reduce the ability of a GAG to induce a HIT response: (i) the nature of the glycosidic bond is unimportant; (ii) the molecule should be unbranched; (iii) the molecule should have a degree of sulfation (i.e., the number of sulfate groups/monosaccharide) of less than 0.60 (i.e., a sulfate to carboxylate (S/C) ratio of no more than 1.2) for chain lengths greater than 10 monosaccharides (i.e., greater than 3000 Daltons); (iv) the molecule should be smaller than 2400 Daltons if its degree of sulfation is 1.0-1.3; and (v) the therapeutic concentration should not exceed 0.12 µg/ml if the degree of sulfation is greater than 0.6 and the chain length greater than 2400 Daltons. See Greinacher et al., "Characterization of the Structural Requirements for a Carbohydrate Based Anticoagulant with a Reduced Risk of Inducing the Immunological Type of Heparin-Associated Thrombocytopenia," *Thromb. Haemost.* (1995) 74: 886-92.

The antigenic complexes formed in HIT are comprised of heparin and releasable platelet proteins, predominantly platelet factor 4 (PF4), a platelet-specific heparin-binding protein. See Greinacher et al., "Heparin-Associated Thrombocytopenia: Isolation of the Antibody and Characterization of a Multimolecular PF4-Heparin Complex as Major Antigen," *Thromb. Haemost.* (1994) 71: 247-51. Heparin and PF4 molecules assemble into a multimolecular antigenic complex. The binding of PF4 to heparin induces the formation of antigenic domains, or neoepitopes, on the PF4 surface that elicit an antibody-mediated immune response. See Li et al., "Defining a Second Epitope for Heparin-Induced Thrombocytopenia/Thrombosis Antibodies Using KKO, a Murine HIT-like Monoclonal Antibody," *Blood* (2002) 99: 1230-36. The immune response is polyclonal and polyspecific with at least three neoepitopes identified based on immunoreactivity studies. See Suh et al., "Antibodies from Patients with Heparin-Induced Thrombocytopenia/Thrombosis Recognize Different Epitopes on Heparin:Platelet Factor 4," *Blood* (1998) 91:916-22.

Antigenic complexes reactive to HIT antibodies can be formed between a variety of negatively charged polyanions and platelet proteins in vitro and in vivo. See U.S. Pat. No. 5,972,718 (Moghaddam et al.), issued Oct. 26, 1999, which discloses the formation of antigenic neoepitopes comprised of polymers bound to PF4 reactive with HIT antibodies, where the polymers can be polyvinyl sulfonate, polystyrene sulfonate, polyanetholesulfonate, polyvinyl phosphate, polyvinyl phosphonate or polyvinyl sulfate comprised of 10-60 subunits having molecular weights between 2000 and 6000; U.S. Pat. No. 5,972,717 (Aster et al.), issued Oct. 26, 1999, which discloses the formation of antigenic neoepitopes reactive with HIT antibodies in which the complexes expressing the antigenic neoepitopes are comprised of PF4 or peptides of PF4 bound to heparin, heparin fragments, heparin salts, heparamine, metallic heparinates, heparin sulfate, chondroitin sulfate, dermatan sulfate and keratan sulfates having preferably 10-20 saccharide residues; U.S. Pat. No. 5,466,582 (Amiral), issued Nov. 14, 1995, which discloses the formation of antigenic neoepitopes reactive with HIT antibodies in which the complexes expressing the antigenic neoepitopes are comprised of PF4, or peptides of PF4 bound to heparin, metal heparinates, heparinoids and heparin fragments, where the heparin fragments have an average molecular weight of less than 6000 Daltons, the heparinoids being selected from the class of heparamine and chondroitin sulfates. Twenty monosaccharides (approximately 6000 Daltons) of chondroitin sulfate represents the minimal chain length that binds PF4 whereas the affinity of chondroitin sulfate for PF4 increases with increased content of the disulfated disaccharide (→4 GlcAβ1→3GalNAc(4,6-O-sulfate) β1→). See Petersen et al., "Characterization of a Neutrophil Cell Surface Glycosaminoglycan that Mediates Binding of Platelet Factor 4," *J. Biol. Chem.* (1999) 274: 12376-82. However, increased sulfation of chondroitin sulfate induces antibodies cross-reactive with the PF4-heparin complex, thrombocytopenia and thrombosis. See Greinacher et al., "Heparin-Associated Thrombocytopenia in a Patient Treated with Polysulphated Chondroitin Sulphate: Evidence for Immunological Crossreactivity between Heparin and Polysulphated Glycosaminoglycan," *Brit. J. Haematol.* (1992) 81: 252-54.

Treatment of HIT usually involves heparin withdrawal and sometimes transfusion. Even so, the failure of early heparin cessation as a treatment for HIT has led to the approval of several direct thrombin inhibitors as alternative anticoagulants. Patients who are positive for the immune complex of heparin-IgG-PF4 or are subject to platelet loss or thrombosis while on heparin therapy are candidates for alternative anticoagulant therapies. Presently the thrombin inhibitors ACOVA™ (argatroban) and Refludan® (recombinant hirudin) are approved for the treatment of HIT/HITT where heparin is contraindicated. These drugs, however, have narrow therapeutic indices, lack antidotes and require laboratory monitoring. Even with the use of these approved drugs, circulating immune complexes may persist for days to weeks and continue to promote the immunohematologic prothrombotic state because these direct thrombin inhibitors do not eliminate all thrombosis associated with HIT. See Bauer et al., supra; http://www.argatroban.com/ref_0.1htm, 2004, supra; Walenga et al., "Combined Thrombin and Platelet Inhibition Treatment for HIT Patients," *Hämostaseologie* (1999) 19:128-33; Greinacher et al., "Lepirudin (Recombinant Hirudin) for Parenteral Anticoagulation in Patients with Heparin-Induced Thrombocytopenia," *Circulation* (1999) 100(6):587-93. As such, the predisposition to life-threatening thrombosis in HIT is neither predictable nor adequately addressed by the alternative use of these direct thrombin inhibitors. Accordingly, despite the use of these alternatives, the morbidity and mortality of HIT patients remains relatively high, and will likely remain so until a therapy is developed that treats the root cause of this disease initiated by the formation and action of the immune complexes in HIT which adversely modulate the functions of platelets, endothelial cells and monocytes.

SUMMARY

One embodiment of this invention is broadly directed at the treatment and/or prevention of heparinoid-induced autoimmune responses, in particular, heparin-induced thrombocytopenia (HIT) and its associated disease states, by using certain dermatan sulfates, as well as certain O-desulfated heparins, separately or in combination, as heparinoid-induced autoimmune response antagonists, and especially as HIT antagonists. The dermatan sulfates of this invention comprise repeating disulfated and/or trisulfated disaccharide units of L-iduronic acid and N-acetyl-D-galactosamine and have the following properties: (1) for at least about 80% of the polysaccharides, a molecular weight in the range of from about 1200 to about 35,000 Daltons; (2) a sulfur content in the range of from about 6 to about 11% (3) a sulfate/carboxylate ratio (S/C) in the range of from about 1.2 to about 2.0; (4) a combined disulfated and trisulfated disaccharide content in the range of from about 20 to 100% by weight of the total disaccharide content; (5) less than about 20% platelet activation activity in the presence of HIT immune sera (HIT sera) or anti-heparin/PF4 antibody (HIT antibody); and (6) an ability to inhibit the activation of human platelets caused by HIT reactive sulfated glycosaminoglycans (GAGs), such as heparin, in the presence of either HIT sera or HIT antibody.

The O-desulfated heparins of this invention comprise heparin molecules selectively O-desulfated at the 2O and/or 3-O positions of the uronic acid and glucosamine saccharide residue, i.e., to provide 2-O- and/or 3-O-desulfated heparins. These O-desulfated heparins have the following properties: (1) an average molecular weight in the range of from about 2000 to about 14,000 Daltons; (2) a sulfate/carboxylate ratio (S/C) in the range of from about 1.2 to about 1.5; (3) a residue on ignition in the range of from about 28 to about 41%; (4) a nitrogen content in the range of from about 1.3 to about 2.5% calculated on a dried basis; (5) a USP antifactor Xa potency of less than about 10 units/mg; (6) a USP heparin potency of less than about 10 units/mg; (7) about 50% or greater inhibitory activity against human leukocyte elastase activity at ratios of O-desulfated heparin:elastase of from about 0.5 to about 1.0; (8) less than about 20% platelet activation activity in the presence of HIT sera or HIT antibody; and (9) an ability to inhibit the activation of platelets caused by HIT reactive sulfated GAGs, such as heparin, in the presence of either HIT sera or HIT antibody.

Another embodiment of this invention is broadly directed at the treatment and/or prevention of heparinoid-induced autoimmune responses, in particular HIT and its associated disease states, by using certain lower molecular weight dermatan sulfates as heparinoid-induced autoimmune response antagonists, and especially as HIT antagonists. These lower molecular weight dermatan sulfates comprise repeating disulfated and/or trisulfated disaccharide units of L-iduronic acid and N-acetyl-D-galactosamine and have the following properties: (1) a mean molecular weight in the range of from about 2000 to about 10,000 Daltons; (2) a sulfur content in the range from about 6.0 to about 11%; (3) a sulfate/carboxylate ratio (S/C) in the range of from about 1.2 to about 2.0; (4) a combined disulfated and trisulfated disaccharide content in the range of from about 20 to 100% by weight of the total disaccharide content; (5) less than about 20% platelet activation activity in the presence of HIT sera or HIT antibody; and (6) an ability to inhibit the activation of platelets caused by HIT reactive sulfated GAGs, such as heparin, in the presence of either HIT sera or HIT antibody.

Direct thrombin inhibitors do not block the activation of platelets caused by complexes of heparin, platelet proteins, and HIT antibodies. While the combined use of a heparin cofactor II agonist, such as dermatan sulfate and various oversulfated derivatives thereof, with a GPIIb/IIIa receptor antagonist have been taught to inhibit thrombin in various thromboembolic disease states, including HIT (see commonly assigned U.S. Pat. No. 6,518,244 (Cardin et al.), issued Feb. 11, 2003), it has been surprisingly found that the dermatan sulfates of this invention by themselves and substantially in the absence of such GPIIb/IIIa receptor antagonists unexpectedly block the platelet activation otherwise caused by immune complexes comprised of heparin, platelet proteins and HIT antibodies, even when substantially in the absence of thrombin. The dermatan sulfates of this invention have been found to disrupt the platelet activation process caused by the immune complexes of HIT, thus abating this disease at its immunological root cause. Also surprising and unexpected is that the potency of this HIT antagonist activity is enhanced by increasing the degree of sulfation and decreasing the molecular weight of these dermatan sulfates, and that this antagonist activity is independent of both glucuronate content and thrombin inhibitory activity.

It has been further surprisingly found that selective O-desulfation of heparin at the 2-O and/or 3-O positions of the uronic acid and glucosamine sugar residues leads to O-desulfated heparin chains with molecular weights typically greater than 2400 Daltons and S/C ratios greater than about 1.0 that, while able to form complexes with platelet proteins, are unable to promote the formation of functional HIT-like immune complexes with anti-heparinoid antibodies that are capable of activating platelets. Not only do the O-desulfated heparins of this invention not form functional autoimmune complexes, but, instead, block the activation of platelets caused by heparin when in the presence of platelet proteins and heparinoid-induced immune sera from HIT patients, and substantially lacking thrombin activity.

The dermatan sulfates and/or O-desulfated heparins of this invention unexpectedly prevent the activation of platelets and endothelial cell damage caused by the immune complexes of HIT, even in the presence of administered heparin, a property or activity referred to as "HIT antagonism." The HIT antagonist properties of the dermatan sulfates and/or O-desulfated heparins of this invention provide a therapeutic modality that not only suppress the autoimmune responses that propagate HIT and its associated disease states by disrupting the communication of immune complexes with platelets and endothelial cells, but also potentially suppresses other disease states that can interfere with the function and longevity of medical devices that interact with or are exposed to blood.

The dermatan sulfates and/or O-desulfated heparins of this invention are useful in the prevention and/or treatment of conditions that occur in response to heparinoid (e.g., heparin) exposure, including elevated immune complexes, heparin-induced platelet activation, thrombocytopenia, the evolution of HIT-specific, platelet-related thrombosis caused by early platelet activation due to these immune complexes (henceforth "thrombosis"), endothelial cell damage due to heparinoid-induced autoimmune responses, as well as the functional impairment of medical devices that are coated with heparinoids or otherwise come into contact with blood where the antigenic complexes of HIT and their immune complexes can form, deposit and potentially build up, such as on stents, catheters, vascular grafts, extracoporeal devices such as heart-lung machines, oxygenators, hemodialysis circuits, filters and membranes, etc., and especially create vascular access obstructions (e.g., in end-stage renal dialysis patients who are routinely exposed to heparin during maintenance hemodialysis). The dermatan sulfates of this invention are also useful in combination with heparin lyases (heparinases) such as heparin lyases I, II and III that degrade heparin to reverse its effects but without affecting the ability of the dermatan sulfates of this invention to treat and/or prevent heparinoid-induced autoimmune responses, especially HIT.

The nonanticoagulant O-desulfated heparins of this invention are also useful when administered to patients suffering from heparinoid-induced autoimmune responses who may be maintained on heparin anticoagulation or alternatively, are anticoagulated by the administration of inhibitors of either thrombin or activated Factor X (FXa), including, for example, DX-9065c (Daiichi Pharm. Ltd.), BAY59-7939 (Bayer), fondaparinux, hirudin (Refludan®), bivalirudin (Angiomax®), argatroban (Argatroban®), etc.

BRIEF DESCRIPTION OF THE DRAWINGS

The invention will be described in conjunction with the accompanying drawings, in which.

DETAILED DESCRIPTION

Figure 1:
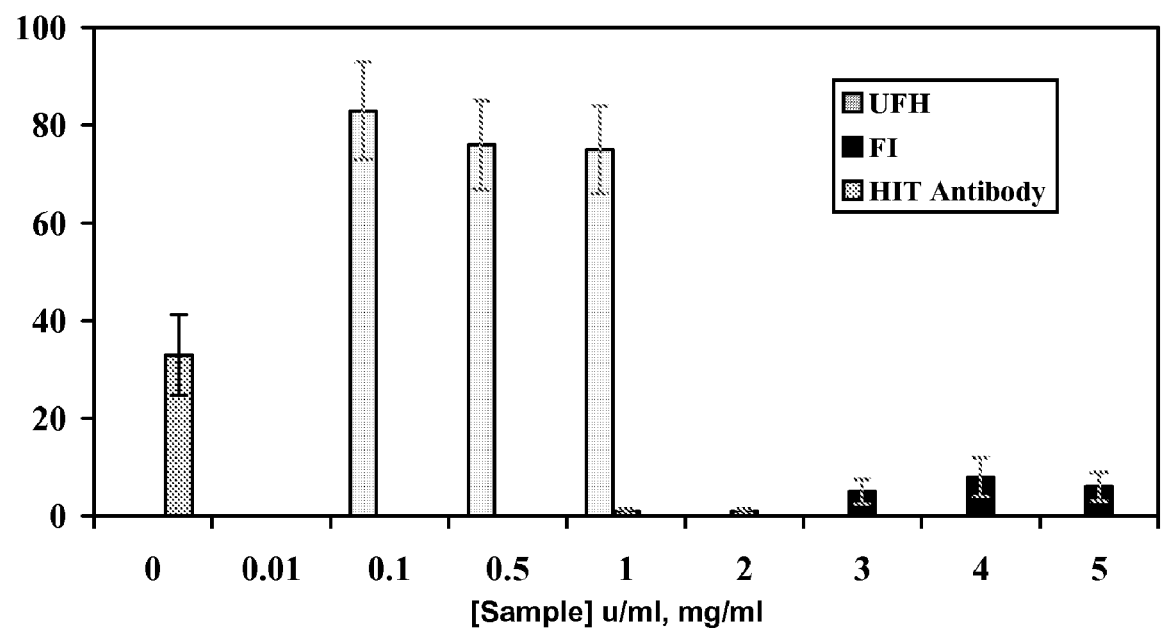
FIG. 1 is a graphical plot of testing of several test samples, at various concentrations, for cross reactivity with heparin antibodies from patients with HIT, as measured by SRA.

It is advantageous to define several terms before describing the invention. It should be appreciated that the following definitions are used throughout this application.

Definitions

Where the definition of terms departs from the commonly used meaning of the term, applicant intends to utilize the definitions provided below, unless specifically indicated.

For the purposes of the present invention, the terms "glycosaminoglycans" or "GAGS" refer interchangeably to the family of sulfated mucopolysaccharides that typically include heparinoids such as heparin, heparin sulfate, chondroitin, chondroitin sulfate, keratan sulfate, dermatan sulfate and their respective derivatives.

For the purposes of the present invention, the term "heparinoid" refers to heparin and other heparin-like GAG polysaccharides, including, but not limited to heparin, heparin fragments, heparin salts, heparamine, metallic heparinates, heparin sulfate, chondroitin sulfates, keratan sulfates, and their respective derivatives.

For the purposes of the present invention, the term "heparinoid-induced autoimmune response" refers to any autoimmune response that is caused by the exposure of an individual to a heparinoid, including immune complex formation resulting from or induced by such responses and subsequent disease states, such as heparin-induced thrombocytopenia. Heparinoid-induced autoimmune responses for which this invention is useful in treating and/or preventing include, but are not limited to: (i) the formation of heparinoid antigenic complexes comprised of a heparinoid and heparinoid-binding protein; (ii) the formation of heparinoid-induced immune complex(es) present in the blood, plasma or serum; (iii) the activation of platelets, endothelium and/or monocytes caused or induced by the presence of heparinoid antigenic complexes and/or heparinoid-induced immune complexes; (iv) thrombocytopenia caused or induced by the presence of heparinoids, heparinoid antigenic complexes, and/or heparinoid-induced immune complexes, with or without platelet and/or fibrin-rich arterial/venous thrombosis; (v) vascular access obstruction caused or induced by the presence of heparinoids, heparinoid antigenic complexes, and/or heparinoid-induced immune complexes, for example, in end-stage renal hemodialysis patients; (vi) the potential impairment of the function and longevity of medical devices that interact with or are exposed to blood from patients who themselves have been exposed to heparinoids, heparinoid antigenic complexes, and/or heparinoid-induced immune complexes; etc.

For the purposes of the present invention, the term "heparin-induced thrombocytopenia" or "HIT" refers broadly to the acquired, heparinoid (typically heparin)-induced immune disease that elicits an autoimmune-antibody type response to circulating and surface-associated antigenic complexes comprised of heparinoid (typically heparin) bound to human platelet proteins, such as platelet factor 4. The immune complexes typically consist of an autoimmune antibody (e.g., anti-heparin antibody) bound to these antigenic complexes that activate platelets via an interaction of the immune complex with the FcγIIa receptor on the platelet surface, or accumulate on and cause damage to the endothelial cell surface.

For the purposes of the present invention, the terms "platelet factor 4" or "PF4" refer interchangeably to a major protein of platelet α-granules that form circulating and surface-associated complexes with heparin, other heparinoids, and other polyanions, and is a non-limiting example of one type of heparinoid-binding protein that when complexed with a heparinoid leads to a heparinoid-induced autoimmune response.

For the purposes of the present invention, the term "polyanions" typically refers to naturally occurring or synthetic polymers that have a net negative charge, interact with platelet proteins, or other heparinoid-binding proteins, that are able to form immune complexes with HIT antibodies, and thereby activate platelets, or interact with other anti-heparinoid-induced antibodies responsible for a heparinoid-induced autoimmune response.

For the purposes of the present invention, the term "UFH" means unfractionated heparin.

For the purposes of the present invention, the term "platelet $^{14}C$ serotonin release assay" or "SRA" refers to the assay involving the measurement of the release of carbon-14 labeled serotonin from human platelets caused by the contact of these platelets with immune complexes comprised of antibodies, platelet proteins and heparinoids.

For the purposes of the present invention, the term "platelet activation activity" refers to the platelet activating activity of a GAG or polyanion as it relates to the ability of various heparinoids and polyanions to form antigenic complexes with platelet proteins and "cross react" with anti-heparinoid antibodies, thus activating human platelets when assessed by the SRA or other suitable test methods that measure the activation of platelets by these immune complexes.

For the purposes of the present invention, the terms "HIT immune sera" and "HIT sera" refer interchangeably to the serum fraction of blood obtained from patients with HIT or other heparinoid-induced immune responses.

For the purposes of the present invention, the terms "anti-heparin antibody," "anti-heparin/PF4 antibody" and "HIT antibody" refer interchangeably to the polyclonal antibodies in the blood of patients, with or without HIT, that are induced as an immune response to the exposure of patients to heparin, other heparinoids, or other polyanions. These terms typically refer to the antibodies that are specifically elicited in response to the antigenic complex(es) caused by GAGs, and their complexes with GAG-binding proteins.

For the purposes of the present invention, the terms "heparin cofactor II (HCII)-dependent anti-IIa activity," "heparin cofactor II activity" and "HCII activity" refer interchangeably to the thrombin inhibitory potency of a sulfated mucopolysaccharide measured in the presence of purified human heparin cofactor II.

For the purposes of the present invention, the term "native dermatan sulfate" usually refers to the sulfated mucopolysaccharide isolated from an animal tissue source comprised of repeating disaccharide units of L-iduronic acid and N-acetyl-D-galactosamine and having a sulfate to carboxylate ratio typically in the range of from about 0.8 to about 1.1.

For the purposes of the present invention, the term "combined disulfated and trisulfated disaccharide content" refers to the combined percentage (by weight) of disulfated disaccharides and/or trisulfated disaccharides, relative to the total disaccharide content (by weight) present in the polysaccharides of the dermatan sulfate.

For the purposes of the present invention, the term "number-average mean molecular weight (Mn)" is defined by the formula $Mn=\Sigma NiMi/\Sigma Ni$, where Ni are the numbers of molecules of molecular weight Mi, as described in Mulloy et al., "Molecular Weight Measurements of Low Molecular Weight Heparins by Gel Permeation Chromatography," *Thrombosis Haemostasis* (1997) 77(4):668-74.

For the purposes of the present invention, the term "weight-average mean molecular weight (Mw)" is defined by the formula $Mw=\Sigma NiMi^2/\Sigma NMi$ in which the terms in this formula are defined as above.

For the purposes of the present invention, the term "mean molecular weight" refers to both the weight-average and number-average mean molecular weights as defined above.

For the purposes of the present invention, the term "average molecular weight" refers to the molecular weight as determined by viscometric methods as described in Liberti et al., "Physiochemical Studies of Fractionated Bovine Heparin II: Viscosity as a Function of Ionic Strength," *Arch. Biochem. Biophys.* (1967) 119:510-18, which is incorporated by reference.

For the purposes of the present invention, the term "$IC_{50}$" means the concentration of a compound that causes 50% inhibition of platelet serotonin release in the SRA when conducted in the presence of HIT serum and Heparin Sodium USP at a 0.1 unit/ml concentration.

For the purposes of the present invention, the terms "heparin-induced autoimmune response antagonist" refers to dermatan sulfates and/or O-desulfated heparins of this invention that can offset, block, inhibit or otherwise ameliorate the disease, disease symptoms and/or disease processes caused by or associated with the heparinoid-induced autoimmune responses, including but not limited to HIT, its antigenic-immune complexes, etc.

For the purposes of the present invention, the term "HIT antagonist" refers to dermatan sulfates and/or O-desulfated heparins of this invention that can offset, block, inhibit or otherwise ameliorate the disease, disease symptoms and/or disease processes typically caused by the activation of platelets by preformed immune complexes comprised of HIT antibodies, a platelet protein(s) and/or a sulfated polysaccharide(s).

For the purposes of the present invention, the term "HIT antagonist activity" refers to the platelet activation inhibitory activity of the dermatan sulfates and/or O-desulfated heparins of this invention, as measured in the SRA in the presence of UFH.

For the purpose of the present invention, the terms "agonist", "HIT agonist" and "HIT agonist activity" refer interchangeably to the platelet activating property of a GAG, heparinoid, or polyanion as determined in the SRA when measured in the absence of any otherwise competing heparinoid, GAG or polyanion.

For the purpose of the present invention, the terms "active ingredient," "active component," "active drug," and "drug" are used interchangeably to refer to pharmaceutical forms of the dermatan sulfates and/or O-desulfated heparins of this invention, alone or in combination with other actives, such as heparin lyases.

For the purposes of the present invention, the terms "heparinase," and "heparin lyase" are used interchangeably to refer to the general class of enzymes that are capable of specifically cleaving the major glycosidic linkages in heparin and heparin sulfate. Three heparin lyases have been identified in Flavobacterium heparinum, a heparin-utilizing organism that also produces exoglycouronidases, sulfoesterases, and sulfamidases that further act on the lyase-generated oligosaccharide products. These lyases are designated as heparin lyase I (heparinase, EC 4.2.2.7), heparin lyase II (heparinase II, no EC number) and heparin lyase III (heparitinase EC 4.2.2.8). The three purified heparin lyases differ in their capacity to cleave heparin and heparin sulfate. Heparin lyase I primarily cleaves heparin; heparin lyase III specifically cleaves heparin sulfate; and heparin lyase II acts equally on both heparin and heparin sulfate. Heparinases useful herein can comprise the individual lyases or mixtures thereof, can be commercially available forms and can include enzymes derived from natural sources, as well as those that have been modified naturally or synthetically to alter their binding affinity and/or catalytic activity. See U.S. Pat. No. 5,567,417 (Sasisekharan et al.), issued Oct. 22, 1996, which is incorporated by reference. Heparin lyses can be used in combination with dermatan sulfates, but not O-desulfated heparins, of this invention.

For the purposes of the present invention, the term "substantially in the absence of a platelet GPIIb/IIIa receptor antagonist" means that dermatan sulfates of this invention are effective to inhibit platelet activation in the absence of a therapeutically effective amount of a platelet GPIIb/IIIa receptor antagonist. Platelet GPIIb/IIIa antagonists include a variety of antibody, antibody fragments, peptides and small molecule compounds that effectively inhibit the expression and/or function of platelet GPIIb/IIIa receptors, as well as their pharmaceutically acceptable salts. Some representative but nonlimiting examples of platelet GPIIb/IIIa antagonists are disclosed in commonly assigned U.S. Pat. No. 6,518,244 (Cardin et al.), issued Feb. 11, 2003.

For the purposes of the present invention, the term "pharmaceutically acceptable salt" means non-toxic salts of the compounds (which are generally prepared by reacting the free acid with a suitable organic or inorganic base) and include, but are not limited to, the acetate, benzalkonium, benzenesulfonate, benzoate, bicarbonate, bisulfate, bitartrate, borate, bromide, calcium, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandlate, mesylate, methylbromide, methylnitrate, methylsulfate, mucate, napsylate, nitrate, oleate, oxalate, pamaote, palmitate, panthothenate, phosphate, diphospate, polygalacturonate, salicylate, stearate, subacetate, succinate, tannate, tartrate, teoclate, tosylate, triethiodide, and valerate salts, as well as mixtures of these salts.

For the purposes of the present invention, the term "medical device" refers to any blood interacting device and/or therapy, including those referred to in 21 CFR §820, that can come into contact with heparinoids, such as heparin, or the immune complexes that are induced to form by such heparinoids. These devices include but are not limited to stents, catheters, vascular grafts, extracoporeal devices and their components, such as heart-lung machines (e.g., cardiopulmonary pumps), drug delivery units (e.g., drug pumps), hemodialysis units, oxygenators, filters, membranes, medical device circuitry, etc.

For the purposes of the present invention, the term "mammal" includes primates (e.g., humans, monkeys, etc.), dogs, rabbits, rats, mice and other species commonly known to be mammals.

For the purposes of the present invention, the term "comprising" means various components and steps can be conjointly employed in the present invention. Accordingly, the term "comprising" encompasses the more restrictive terms "consisting essentially of" and "consisting of."

For the purposes of the present invention, all amounts, parts, ratios and percentages used herein are by weight unless otherwise specified.

DESCRIPTION

1. Dermatan Sulfates and Methods of Preparing Same

The dermatan sulfates useful in this invention comprise repeating disulfated and/or trisulfated disaccharide units of L-iduronic acid and N-acetyl-D-galactosamine. These disulfated and/or trisulfated disaccharide units are generally represented by the following formula:

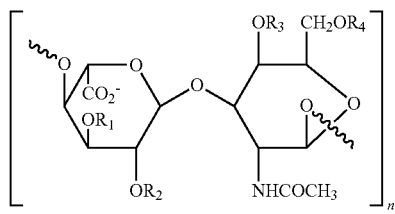

wherein n is typically in the range of from about 3 to about 60 for at least about 80% of the polysaccharide chains; wherein $R_1$, $R_2$, $R_3$, and $R_4$ can be H or $SO_3$; and wherein at least two of $R_1$, $R_2$, $R_3$, and $R_4$ are $SO_3^-$. These include 4,6-disulfated species ($R_3$ and $R_4$ are $SO_3^-$), 2,4-disulfated species ($R_2$ and $R_3$ are $SO_3^-$), 2,3-disulfated species ($R_1$ and $R_2$ are $SO_3^-$), 2,6 disulfated species ($R_2$ and $R_4$ are $SO_3^-$), 3,4 disulfated species ($R_1$ and $R_3$ are $SO_3^-$), 2,4,6-trisulfated species ($R_2$, $R_3$ and $R_4$ are $SO_3^-$), 2,3,4-trisulfated ($R_1$, $R_2$ and $R_3$ are $SO_3^-$), 2,3,6-trisulfated species ($R_1$, $R_2$ and $R_4$ are $SO_3^-$), and 3,4,6-trisulfated species ($R_1$, $R_3$ and $R_4$ are $SO_3$), wherein the trisulfated species are no more than about 20% of the total disaccharide content. The dermatan sulfates of this invention usually comprise the 4,6-disulfated, 2,4-disulfated, and/or 2,4,6-trisulfated species, and typically with no more than about 20%, more typically no more than about 15%, of the total disaccharide content being the 2,4,6-trisulfated species.

These dermatan sulfates also have the following general properties: (a) an increased content of O-sulfated moieties relative to native dermatan sulfate; (b) an affinity for PF4 without appreciably inducing antigenic neoepitope expression that causes cross-reactivity with HIT antibodies; and (c) the ability to inhibit the activation of platelets by immune complexes comprised of heparin, platelet proteins and HIT antibodies from HIT patients. In particular, dermatan sulfates useful in this invention specifically have the following chemical, physical and physiological properties: (1) a molecular weight in the range of from about 1200 to about 35,000 Daltons; (2) a sulfur content in the range from about 6 to about 11%; (3) a sulfate/carboxylate ratio (S/C) in the range of from about 1.2 to about 2.0; (4) a combined disulfated and trisulfated disaccharide content of from about 20 to 100%; (5) less than about 20% platelet activation activity in the presence of HIT (e.g., human) sera or HIT antibody at concentrations of 0.001-1 mg/ml in the absence of added heparin, as measured in vitro in the SRA; (6) an ability to inhibit the activation of human platelets caused by HIT reactive sulfated GAGs, such as heparin, in the presence of either HIT sera or HIT antibody, as measured in vitro in the SRA; (7) an ability to inhibit P-selectin expression and microparticle formation of human platelets induced by immune complexes of heparin, platelet proteins and HIT sera; (8) an $IC_{50}$ of less than about 250 μg/ml in the presence of added Heparin Sodium USP at 0.1 u/ml, as measured in vitro in the SRA; and (9) optionally a heparin cofactor II activity of at least about 15 u/mg, and typically in the range of from about 20 to about 130 u/mg. Particularly desirable dermatan sulfates have the following chemical, physical and physiological properties: (2) a sulfur content of from about 8 to about 11%; (3) a sulfate/carboxyl ratio of from about 1.45 to about 2.0; (4) a combined disulfated and trisulfated disaccharide content of from about 45 to 100%; (5) no more than about 20% of the total disaccharide content being trisulfated disaccharides; (6) less than about 20% platelet activation activity (as previously defined); (7) an ability to inhibit the activation of human platelets (as previously defined); (8) an ability to reduce P-selectin expression and microparticle formation of human platelets (as previously defined); (9) an $IC_{50}$ of less than about 150 μg/ml (as previously defined); and (10) a heparin cofactor II activity of from about 60 to about 130 u/mg.

Another embodiment of the dermatan sulfates useful in this invention are certain low molecular weight dermatan sulfates (LMWDS) that also comprise repeating disulfated and/or trisulfated disaccharide units of L-iduronic acid and N-acetyl-D-galactosamine. The LMWDS embodiments of this invention have the following general properties: (1) an affinity for PF4 without appreciably inducing antigenic neoepitope expression that leads to cross-reactivity with HIT antibodies; and (2) the ability to inhibit the activation of platelets by immune complexes comprised of heparin, platelet proteins and HIT antibodies from HIT patients. These LMWDS embodiments of this invention also have improved HIT antagonist properties, as well as subcutaneous bioavailabilities.

The LMWDS embodiments of this invention specifically have the following chemical, physical and physiological properties: (1) a mean molecular weight in the range of from about 2000 to about 10,000 Daltons; (2) typically at least about 50% of the polysaccharide chains having molecular weights of from about 2000 to about 10,000 Daltons; (3) a ratio of the weight average mean molecular weight to the number average mean molecular weight of from about 1.2 to about 1.8; (4) a sulfur content of from about 6 to about 11%; (5) a sulfate/carboxyl ratio of from about 1.2 to about 2.0; (6)

a combined disulfated and trisulfated disaccharide content of from about 20 to 100%; (7) less than about 20% platelet activation activity in the presence of HIT (e.g., human) sera or anti-heparin/PF4 antibody (HIT antibody) at concentrations of 0.001-5 mg/ml in the absence of added heparin, as measured in vitro in the SRA; (8) an ability to inhibit the activation of human platelets caused by HIT reactive sulfated GAGs in the presence of either HIT sera or HIT antibody, as measured in vitro in the SRA; (9) an ability to inhibit P-selectin expression and microparticle formation of human platelets induced by immune complexes of heparin, platelet proteins and HIT sera; (10) an $IC_{50}$ of less than about 150 μg/ml in the presence of added Heparin Sodium USP at 0.1 u/ml, as measured in vitro in the SRA; and (11) optionally a heparin cofactor II activity of greater than about 15 u/mg. Particularly desirable LMWDS embodiments of this invention have the following chemical, physical and physiological properties: (1) a mean molecular weight in the range of from about 3500 to about 8500 Daltons; (3) a ratio of the weight average molecular weight to the number average molecular weight of from about 1.3 to about 1.6; (4) a sulfur content of from about 8 to about 11%; (5) a sulfate/carboxyl ratio of from about 1.45 to about 2.0; (6) from about 45 to 100% of the total disaccharide content being disulfated disaccharides; (7) no more than about 20% of the total disaccharide content being trisulfated disaccharides; (8) less than about 20% platelet activation activity (as previously defined); (9) an ability to inhibit the activation of human platelets (as previously defined); (10) an ability to reduce P-selectin expression and microparticle formation (as previously defined); (11) an $IC_{50}$ of less than about 100 μg/ml (as previously defined), more typically less about 50 μg/ml, most typically less about 25 μg/ml; and (12) a heparin cofactor II mediated inhibition of thrombin activity of greater than about 15 u/mg.

The chemical, physical and physiological properties of the dermatan sulfates, including the LMWDS embodiments, of this invention can be determined by the following methods:

a. Molecular weight. By gel permeation chromatography according to the method of and as defined by van Dedem et al., "Determinations of the Molecular Mass of Low Molecular Mass (LMM) Heparin," *Pharmeuropa* (1991) 3:202-225 (herein incorporated by reference), using the $1^{st}$ International Reference Standard for Low Molecular Weight Heparin (90/868) as the calibrant. Average molecular weights. By viscometric methods as described by Liberti et al., "Physiochemical Studies of Fractionated Bovine Heparin II: Viscosity as a Function of Ionic Strength," *Arch. Biochem. Biophys.* (1967) 119: 510-18 (herein incorporated by reference).

b. Sulfur content. By the following procedure: Approximately 500 mg of glycosaminoglycan is accurately weighed and oxidized with 50 ml aqua regia by heating slowly for 15-30 minutes. Next, 50 ml of water is carefully added and heated to boiling. Then, 10 ml of 30% barium chloride solution is added to precipitate the sulfur as barium sulfate. The mixture is brought to a boil, allowed to cool and filtered on a previously heated and weighed filtering crucible. The filtrate is washed with purified water until the wash tests negative for chlorides pursuant to USP 26 <221> 2056. The crucible is then placed in a vacuum oven at 90-100° C. for 1 hour and transferred to a dessicator and allowed to cool before weighing. The % sulfur is determined from the weight of barium sulfate.

c. Sulfate/carboxylate ratio. According to Ph. Eur. 1997: 0828.

d. Anti-IIa Activity. Performed in a plasma-free system with purified α-thrombin (Lot No. HT2450PRA, 3025 NIH u/mg; Enzyme Research Laboratories, South Bend Ind.) in either the presence of purified human HCII as described in U.S. Pat. No. 5,922,690 (Van Gorp et al.), issued Jul. 13, 1999 (herein incorporated by reference) or purified human antithrombin III (Lot No. HAT 860; Enzyme Research Laboratories, South Bend Ind.) using chromogenic substrate Pefachrome® TH (Pefa-5114) H-D-cyclohexylglycyl-alanyl-arginine-para-nitroanilide diacetate (Centerchem, Inc., Norwalk Conn.). Measurements can be performed manually or on an ACL 300 Plus Analyzer (Instrumentation Laboratory, Lexington Mass.) and anti-factor IIa activity calculated based on the USP Heparin Reference Standard K-5 (U.S. Pharmacopeial Convention, Inc., Rockville Md.).

e. SRA. According to the method described in Walenga et al., "Laboratory Tests for the Diagnosis of Heparin-Induced Thrombocytopenia," *Semin. Thromb. Hemost.* (1999) 25(Suppl 1): 43-49 (herein incorporated by reference).

f. Heparin Assay. Performed as described in the United States Pharmacopoeia (USP) 26:898.

g. Anti-factor Xa activity. Performed as described in the United States Pharmacopoeia (USP) 26:897-8.

h. HIT-reactive antigen complexes. Quantified by the PF4 ENHANCED® ELISA kit (Cat. No. X-HAT 45) according to the manufacturer's instructions (GTI, Waukesha Wis.).

The dermatan sulfates of this invention can be prepared by the oversulfation of native dermatan sulfate. For example, these dermatan sulfates can be prepared by sulfation of native dermatan sulfate using a sulfur trioxide:trimethylamine complex in a suitable organic solvent such as formamide. Methods of preparing such dermatan sulfates are disclosed in U.S. Pat. No. 5,922,690 (Van Gorp et al.), issued Jul. 13, 1999, which is incorporated by reference, and which describes oversulfation of native dermatan sulfate to provide yields of greater than about 75% 4,6 di-O-sulfated species; species having lower and higher degrees of sulfation can also be useful herein and can be obtained by optimizing reaction conditions appropriately by techniques well known to those skilled in the art. More extensive sulfation to include other sites can also be desirable. See Pavão et al., "Highly Sulfated Dermatan Sulfates from Ascidians: Structure versus Anticoagulant Activity of these Glycosaminoglycans," *J. Biol. Chem.* (1998) 273:27848-57, which is incorporated by reference. Optimization of the (HIT) antagonist properties can be realized by varying such parameters as reactant chemistries that include the use of quaternary salts to mask or restrict, and therefore to control or redirect sulfation sites as well as the extent of sulfation in a organic solvent medium, by varying the ratio of reactants, by varying the reaction temperatures and times, and the like. These sulfation products can be further fractionated, for example, by ion exchange methods, to obtain mixtures that differ in their degree of sulfation and therefore their (HIT) antagonist properties. Native dermatan sulfate itself can also be fractionated by such methods to yield higher sulfated mixtures having (HIT) antagonist properties as previously described. Alternatively, the dermatan sulfates of this invention can be obtained by de novo synthesis using protection-deprotection strategies well known to those skilled in the art of solution- and solid-phase synthesis chemistries.

The LMWDS embodiments of this invention can be prepared by any number of approaches including, but not limited to: (i) the oversulfation of native dermatan sulfate, followed by controlled depolymerization; (ii) controlled depolymerization of native dermatan sulfate, followed by oversulfation of the fragments; (iii) depolymerization of native dermatan sulfate followed by the enrichment of the di- and tri-sulfated disaccharide-containing oligosaccharide species by ion exchange fractionation; and (iv) synthesis in solution or on solid-phase supports such resins. Depolymerization of native dermatan sulfate or oversulfated dermatan sulfate can be achieved by a variety of techniques well known to those skilled in the art, including but not limited to: (v) periodate oxidation, followed by borohydride reduction and acid hydrolysis; (vi) β-elimination of a benzyl esterified dermatan sulfate or oversulfated dermatan (or other suitable ester) in an alkaline media from which the ester is prepared from its respective quaternary ammonium salt (e.g., benzethonium dermatan); (vii) peroxidative depolymerization; (viii) nitrous acid degradation; (ix) the action of chondroitinase enzymes, (x) gamma irradiation, or (xi) suitable combinations of methods (v)-(x). See, for example, WO 93/05075 (Mascellani et al.), published Mar. 18, 1993 and WO 98/55514 (Lundqvist et al.), published Dec. 10, 1998 (herein incorporated by reference) which describe the depolymerization of mammalian dermatan sulfate by acid cleavage of periodate oxidized and sodium borohydride reduced dermatan sulfate, with the enrichment of the oversulfated fractions by ion exchange fractionation.

Representative methods of depolymerization of native dermatan sulfate or oversulfated dermatan sulfate to provide the LMWDS embodiments of this invention include, for example, β-eliminative degradation of sulfated heteropolysaccharides as described in Kiss, "β-Eliminative Degradation of Carbohydrates Containing Uronic Acid Residues," *Adv. Carbohydr. Chem. Biochem.*, (1974) 29: 229-303, as well as U.S. Pat. No. 5,389,618 (Debrie), issued Feb. 14, 1995; European Patent Application 0040144 (Mardiguian), published Nov. 18, 1981; and Irish Patent 51283 (Pharmuka Laboratoire), published Nov. 26, 1986, (alkaline dependent β-elimination of heparin benzylic esters to yield low molecular mass heparins), all of which are incorporated by reference. Other methods for preparing either mono- or polydisperse LMWDS embodiments of this invention include those disclosed in, for example, U.S. Pat. No. 4,987,222 (De Ambrosi et al.), issued Jan. 22, 1991 (gamma irradiation-induced depolymerization of GAGs); U.S. Pat. No. 4,757,057 (Fussi et al.), issued Jul. 12, 1988 (peroxidative depolymerization); Shaklee et al., "The Disaccharides Formed by Deaminative Cleavage of N-Deacetylated Glycosaminoglycans," *Biochem J.* (1986) 235:225-36 (de-N-acetylation by hydrazinolysis followed by limited depolymerization with nitrous acid at pH 4.0); U.S. Pat. No. 6,093,563 (Bennett et al.), issued Jul. 25, 2000 (action of chondroitinases); U.S. Pat. No. 4,943,630 (Jacquinet), issued Jul. 24, 1990 (discrete synthesis of galactosamine-uronic acid-containing oligosaccharides); (U.S. Pat. No. 6,846,917 (Seeberger et al.), issued Jan. 25, 2005 (solid-phase and solution phase synthesis of heparin and other GAGs); U.S. Pat. No. 6,579,725 (Seeberger et al.), issued Jun. 17, 2003 (linkers for synthesis of oligosaccharides on solid supports), all of which are incorporated by reference.

2. O-Desulfated Heparins and Methods of Preparing Same

The O-desulfated heparins useful in this invention comprise heparin molecules that have been selectively O-desulfated at the 2-O and/or 3-O positions of the uronic acid (i.e., either L-iduronic acid or D-glucuronic acid) and glucosamine saccharide residues to provide 2-O- and/or 3-O-desulfated heparins. See, for example, FIG. 2 of U.S. Pat. No. 5,668,118 (Kennedy), issued Sep. 16, 1997, which shows a 2-O-desulfated saccharide residue. The O-desulfated heparins useful in this invention have the following properties: (1) an average molecular weight within the range of from about 2000 to about 14,000 Daltons; (2) a sulfate/carboxylate ratio (S/C) within the range of from about 1.2 to about 1.5; (3) a residue on ignition within the range of from about 28 to about 41%; (4) a nitrogen content within the range of from about 1.3% to about 2.5% (calculated on a dried basis); (5) a USP antifactor Xa potency of less than about 10 units/mg; (6) a USP heparin potency of less than about 10 units/mg; (7) about 50% or greater inhibitory activity against human leukocyte elastase activity at ratios of O-desulfated heparin:elastase of from about 0.5 to about 1.0; (8) less than about 20% platelet activation activity in the presence of HIT sera or HIT antibody over a concentration range from about 0.001-1.0 mg/ml; and (9) an ability to inhibit the activation of platelets caused by HIT reactive sulfated GAGs, such as heparin, in the presence of either HIT sera or HIT antibody at $IC_{50}$ values of less than about 150 μg/ml, more typically less than about 50 g/ml, and most typically less than about 25 g/ml.

The chemical, physical and physiological properties of the O-desulfated heparins of this invention can be determined by the following methods:

a. Molecular weight. By viscometric methods as described by Liberti et al., "Physiochemical Studies of Fractionated Bovine Heparin II: Viscosity as a Function of Ionic Strength," *Arch. Biochem. Biophys.* (1967) 119:510-18 (herein incorporated by reference).

c. Sulfate/carboxyl ratio. According to Ph. Eur. 1997:0828.

d. SRA. According to the method described in Walenga et al., "Laboratory Tests for the Diagnosis of Heparin-Induced Thrombocytopenia," *Semin. Thromb. Hemost.* (1999) 25(Suppl 1): 43-49 (herein incorporated by reference).

e. Tests for the Diagnosis of Heparin-Induced Thrombocytopenia,"

f. *Semin. Thromb. Hemost.* (1999) 25(Suppl 1): 43-49 (herein incorporated by reference).

g. Heparin Assay. Performed as described in the United States Pharmacopoeia (USP) 26:898.

h. Anti-factor Xa activity. Performed as described in the United States Pharmacopoeia (USP) 26:897-8.

i. Residue on ignition. <281> USP 26.

j. Nitrogen (dry basis). Method I<461> USP 26.

i. HIT-reactive antigen complexes. Quantified by the PF4 ENHANCED® ELISA kit (Cat. No. X-HAT 45) according to the manufacturer's instructions (GTI, Waukesha Wis.).

j. Human leukocyte elastase (HLE.). According to the method described in Fryer et al., "Selective O-desulfation Produces Nonanticoagulant Heparin that Retains Pharmacological Activity in the Lung," *J. Pharmacol. Exp. Ther.* (1997) 282: 208-19 (herein incorporated by reference).

The O-desulfated heparins of this invention may be prepared from high potency heparins of either porcine or bovine origins having USP heparin potencies of greater than about 140 USP units/mg or from low molecular weight heparins as starting materials. Procedures for preparing the O-desulfated heparins of this invention are disclosed in, for example, U.S. Pat. No. 5,296,471 (Holmes et al.), issued Mar. 22, 1994, U.S. Pat. No. 5,668,118 (Kennedy), issued Sep. 16, 1997; U.S. Pat. No. 5,707,974 (Kennedy), issued Jun. 13, 1988; U.S. Pat. No. 5,808,021 (Holmes et al.), issued Sep. 15, 1998; U.S. Pat. No. 5,990,097 (Kennedy), issued Nov. 23, 1999; U.S. Pat. No. 5,912,237 (Kennedy), issued Jun. 5, 1999; and U.S. Pat. No. 6,077,683 (Kennedy), issued Jun. 20, 2000, the relevant portions of all of which are herein incorporated by reference.

3. Uses of Dermatan Sulfate and/or O-Desulfated Heparins, Methods for Administering and Pharmaceutical Compositions Containing Same The dermatan sulfates and/or O-desulfated heparins of this invention are useful in the treatment of patients having or potentially susceptible to heparinoid-induced immune responses, such as HIT and its associated disease states (e.g., conditions of elevated immune complexes that occur in response to heparin exposure), with or without associated thrombosis, and even when administered substantially in the absence of a platelet glycoprotein IIb/IIIa receptor antagonist. The dermatan sulfates and/or O-desulfated heparins of this invention are also useful in blocking the ability of antigenic complexes comprised of heparin, platelet proteins and other HIT antibodies to activate human platelets, as measured by SRA.

More specifically, the dermatan sulfates and/or O-desulfated heparins of this invention are useful therapeutically for the treatment and/or prevention of disease states characterized by an autoimmune response to heparin and other heparinoid therapies where the afflicted patient experiences a rise in antibodies reactive to antigenic complexes of heparin (or other heparinoids) and associated platelet proteins where the condition can progress to a pronounced thrombocytopenia, typically characterized clinically as a greater than about 50% fall in platelet numbers or a nadir count of less than about 100,000 µl. The dermatan sulfates and/or O-desulfated heparins of this invention have particular efficacy in treating the underlying cause of HIT by suppressing the activation of platelets, endothelial cells, or monocytes caused by circulating and bound immune complexes comprised of heparin, platelet proteins and HIT antibodies, thereby reducing the immunoreactive, inflammatory and procoagulant states of HIT characterized by activation of platelets, endothelium, monocytes and thrombin generation known to be elevated in HIT, as well as treating and/or preventing vascular access obstruction associated with such immune complexes comprised of heparin, platelet proteins and anti-heparin antibodies experienced by, for example, hemodialysis patients.

The dermatan sulfates and/or O-desulfated heparins of this invention can be administered in any manner suitable to deliver the active ingredient(s) to the patient and/or medical device to treat and/or prevent heparinoid-induced autoimmune responses, by reaching the antigenic and receptor sites of the patient, or the surfaces of medical devices that interact with or are exposed to blood from a patient who is also exposed to heparinoids, that can promulgate a systemic or localized disease process or device impairment or failure(s). Thus, the dermatan sulfates and/or O-desulfated heparins of this invention may be administered in the presence of heparinoids, or administered with heparin in those situations where heparin administration alone is otherwise contraindicated.

In the case of medical devices, the dermatan sulfate sulfates and/or O-desulfated heparins of this invention can be used to treat the device before or after exposure of the patient to the heparinoids. The medical devices can also be provided with a source of the dermatan sulfates and/or O-desulfated heparins of this invention to be delivered to the device to minimize or prevent such impairment. For example, the medical device can be coated with the dermatan sulfates and/or O-desulfated heparins of this invention (e.g., as a sustained release coating of the dermatan sulfates to minimize or prevent the aftermath of heparinoid-induced autoimmune responses from eventually clogging, fouling or otherwise obstructing the device, and thus causing impairment or failure thereof.

For administration to patients (e.g., humans), the dermatan sulfates and/or O-desulfated heparins of this invention can be in the form of injectable or oral compositions for administration. Suitable injectable compositions for use in this invention can be given intravenously, parenterally, intramuscularly, or subcutaneously and include bolus or extended infusion compositions. Injectable administration of the dermatan sulfates and/or O-desulfated heparins of this invention typically involves the preparation of suitable infusion solutions according to procedures well known to those skilled in the pharmaceutical arts. Administration in these various ways are suitable as long as the beneficial pharmaceutical effect of the dermatan sulfates and/or O-desulfated heparins of this invention is realized by the patient. Such beneficial effect is usually achieved when the target plasma level concentrations of the active drug are maintained. Such target plasma level concentrations can be readily determined for each patient by physicians and veterinarians skilled in the art.

The dosage regimen for the dermatan sulfate and/or O-desulfated heparins is selected in accordance with a variety of factors, including type, species, age, weight, sex and medical condition of the patient; the severity of the condition to be treated or prevented; the routes of administration; the renal and hepatic function of the patient; and the particular dermatan sulfate and/or O-desulfated heparin to be used. An ordinarily skilled physician or veterinarian can readily determine and prescribe the therapeutically effective amount of the dermatan sulfate and/or O-desulfated heparin required to prevent, counter, or arrest the progress of the heparinoid-induced autoimmune response condition or disease state, such as HIT. For example, in the case of LMWDS HIT antagonists of this invention, therapeutic doses will typically be in the range of from about 0.1 to about 250 mg/kg (as an intravenous or subcutaneous bolus), followed by a maintenance intravenous infusion as is needed of from about 5 to about 600 microg/kg/min.

The dermatan sulfates and/or O-desulfated heparins of this invention can be administered in admixture with suitable pharmaceutical diluents, excipients or carriers (collectively referred to hereinafter as "pharmaceutical carriers"), suitably selected with respect to the intended form of administration, such as oral tablets, capsules, elixirs, syrups and the like, and consistent with conventional pharmaceutical practices. See, for example, Remington, *The Science and Practice of Pharmacy* (2000, 20$^{th}$ Ed., Mack Publishing Company) (herein incorporated by reference) for suitable pharmaceutical carriers well known to those skilled in the art. Injectable compositions suitable for use in this invention are well known to those skilled in the pharmaceutical arts. For example, injectable compositions can include aqueous solutions, syrups, aqueous or oil suspensions and emulsions with edible oil, including cottonseed oil or peanut oil. Suitable dispersing or suspending agents for aqueous suspensions include synthetic or natural gums, such as tragacanth, alginate, acacia, dextran, sodium carboxymethyl cellulose, gelatin, methylcellulose and polyvinylpyrrolidone. These injectable compositions can include a sterile aqueous or nonaqueous solvent, in particular water, isotonic saline, isotonic glucose solution, buffer solution or other solvent conveniently used for parenteral administration of active pharmaceutical ingredients, or can be provided as a sterile freeze-dried powder, which is readily dissolved in a sterile medium immediately prior to use. The injectable compositions of this invention can be formulated as long acting depot preparations for subcutaneous or intramuscular implantation, and can include suitable polymeric or hydrophobic emulsions in the pharmaceutical carrier.

Typically, suitable injectable (e.g., intravenous) solutions include pharmaceutically acceptable pH buffers (e.g., sodium citrate), tonicity adjusting agents and other components providing a storage stable and therapeutically effective injectable solution. Tonicity adjusting agents, including sodium chloride, are used to adjust tonicity for osmotic pressure and to prevent blood cell lysing. These agents minimize pain and thrombophlebitis often experienced by patients receiving intravenous administrations of pharmaceutical compositions. The amount used is that which makes the formulation isotonic with the osmotic pressure of the biological system of the patient. Expressed in osmolarity units, the preferred amounts of tonicity adjusting agent suitable for use in the present invention (e.g., sodium chloride) are from about 50 to about 500 milliosmoles, more preferably about 290 milliosmoles. For injectable compositions, pharmaceutically acceptable osmolarity can be achieved by formulating with an amount of sodium chloride of from about 1.5 to about 15 mg/ml, preferably about 9 mg/ml. Such osmolality can also be achieved by using an amount of mannitol of from about 7 to about 75 mg/ml, preferably about 50 mg/ml. Other tonicity adjusting agents which can be used to adjust tonicity include, but are not limited to, dextrose and other sugars. These injectable compositions can also be suitable for long-term storage in glass containers commonly used in the pharmaceutical industry, e.g., in concentrated form in standard USP Type * borosilicate glass containers.

In general, the method for preparing injectable compositions comprising the dermatan sulfate and/or O-desulfated heparin involves combining the various ingredients in a mixing vessel, e.g., at room temperature. The active ingredients (in salt or free base form), buffers sources (e.g., citric acid and sodium citrate), and tonicity adjusting agent(s), are combined to obtain an active ingredient concentration typically in the range of from about 0.01 mg/ml to about 1 mg/ml. In one embodiment for preparing such compositions, a substantial portion of the finished product amount of water (for example, from about 60 to 100%) is introduced into a standard pharmaceutical mixing vessel. An amount of the dermatan sulfate and/or O-desulfated heparin suitable for obtaining the desired finished product concentration is dissolved in the water. Amounts of sodium citrate and citric acid sufficient to obtain a finished citrate concentration of from about 2 to about 20 mM, are added. A pharmaceutically acceptable amount of tonicity adjusting agent in the isotonic range is added. Any remaining portion of water is then added to achieve the desired final concentrations of ingredients. The amount of water initially used in preparing the formulation, and the amount of the remaining portion of water added at the end of the procedure, does not affect the properties of the finished product. Such amounts are a matter of choice for those skilled in the pharmaceutical arts, allowing for pH adjustment during formulation. Concentrated formulations of these injectable compositions can be diluted at the time of administration with a suitable diluent to obtain a finished concentration, for example, of about 0.05 mg/ml, which is suitable for transfer to an infusion bag and use by a patient in need of the treatment.

The dermatan sulfates and/or O-desulfated heparins of this invention that are orally active can be administered as oral dose forms as tablets, capsules, including sustained or controlled release formulations, pills, powders, granules, elixirs, tinctures, suspensions, syrups and emulsions, can be administered one or more times during the day, e.g., one, two, three or four times daily. For oral administration in the form of a tablet or capsule, the dermatan sulfate can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like. For oral administration in liquid form, the oral drug components can be combined with any oral, non-toxic, pharmaceutically acceptable inert carrier such as ethanol, glycerol, water and the like. Suitable carriers for oral administration include but are not limited to amino acid compounds of the type disclosed in U.S. Pat. No. 5,650,386 (Leone-Bay et al.), issued Jul. 22, 1997 and U.S. Pat. No. 5,965,121 (Leone-Bay et al.), issued Oct. 12, 1999, both of which are incorporated by reference. Moreover, when desired or necessary, suitable binders, lubricants, disintegrating agents and coloring agents can also be incorporated into the mixture. Suitable binders include starch, gelatin, natural sugars such as glucose or β-lactose, corn-sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

Oral compositions with enteric coatings can be prepared by mixing the dermatan sulfate and/or O-desulfated heparin with an excipient to form a spheroid, and coating the spheroid with a thin polymer film. For example, the dermatan sulfate and/or O-desulfated heparin can be mixed with non-water swellable microcrystalline cellulose to form a spheroid which is then coated with a film of hydroxypropyl methyl cellulose phthalate and or a plasticizer which prevents any release of the active ingredient in the stomach. When the composition reaches the intestine, the dermatan sulfate and/or O-desulfated heparins is then released. Other suitable materials for enteric coatings include, for example, hydroxypropyl methyl cellulose acetate succinate, hydroxypropyl methyl cellulose hexahydrophthalate, shellac, cellulose acetate, cellulose acetate phthalate, polyvinyl acetate phthalate, carboxymethyl ethyl cellulose, methacrylic acid copolymers, methacrylic ester copolymers and the like.

Oral compositions can also be prepared by mixing the dermatan sulfate and/or O-desulfated heparin with a wetting agent such as fatty acid esters, lecithin, sucrose, mannitol or sorbitol and then spheronizing or granulating the mixture into microgranules. These are then coated with a microporous membrane polymer such as Eudragit® E30D (Rohm Pharma GmbH, Weiterstadt, Germany), hydroxypropyl methyl cellulose phthalate and other wetting agents, plasticizers and the like. These formulations are enteric by nature and the dermatan sulfate does not become bioavailable until the system reaches the intestine.

Oral compositions can also be prepared by mixing the dermatan sulfate and/or O-desulfated heparin and an acid such as fumaric or tartaric acid which is compressed into a spherical tablet and coated with lacquers that are insoluble in gastric juices but soluble in intestinal juices. These lacquers include copolymers of acrylic acid and methacrylic acid esters. The acidic matrix prevents quick dissolution early and yet promotes the active ingredient's bioavailability further downstream in the digestive tract.

Oral compositions can also be prepared by coating a solid dosage form of the dermatan sulfate and/or O-desulfated heparin with hydroxypropyl methyl cellulose phthalate or acidic succinyl and acetyl esters of hydroxypropyl methyl cellulose. Triethylcitrate is added as a plasticizer which aids in the binding of the coating material to the core pellet. The coating resists dissolution in the stomach but completely dissolves in the small intestine.

In general, solid dosage forms comprising the dermatan sulfate and/or O-desulfated heparin can be coated using conventional coating techniques such as conventional pan coating techniques or column spray coating techniques. See PCT application WO 99/38827 (Cook et al.), published Aug. 5, 1999 (herein incorporated by reference) for a more detailed description of these techniques. The dermatan sulfate and/or O-desulfated heparin can also be administered in the form of liposome delivery systems, such as small unilamellar vesicles, large unilamellar vesicles and multilamellar vesicles. The liposomes can be formed from a variety of phospholipids, such as cholesterol, stearylamine or phophatidylcholines. The dermatan sulfate and/or O-desulfated heparin can also be delivered using monoclonal antibodies as individual carriers to which the active ingredient molecules are coupled or the active ingredients can be coupled with soluble polymers as targetable drug carriers. These soluble polymers include polyvinylpyrrolidone, pyran copolymer, polyhydroxy-propyl-methacrylamide-phenol, polyhydroxyethyl-aspartamide-phenol, or polyethyleneoxide-polylysine substituted with palmitoyl residues. In addition, the active ingredients can be coupled to biodegradable polymers that control the release of the active ingredient, for example, polylactic acid, polyglycolic acid, copolymers of polylactic and polyglycolic acid, polyepsilon caprolactone, polyhydroxy butyric acid, polyorthoesters, polyacetals, polydihydropyrans, polycynacrylates and cross-linked or amphiphatic block copolymers of hydrogels.

The dermatan sulfate and/or O-desulfated heparin can also be formulated as ocular eye drops. See PCT application WO 99/38827 (Cook et al.), published Aug. 5, 1999 (herein incorporated by reference) for a more detailed description of the other ingredients in ocular eye drop formulations, suitable dosing schemes for such formulations and methods for preparing such formulations. Suitable eyedrop formulations are those which are isotonic and maintain sufficient contact with the eye surface to systemically deliver the active ingredient to the patient. The ocular preparation can be a solid insert, such as one which, after dispensing the active ingredient, remains essentially intact, or a bioerodible insert that is soluble in lacrimal fluids, or otherwise disintegrates. See PCT application WO 99/38827 (Cook et al.), published Aug. 5, 1999 (herein incorporated by reference) for a more detailed description of solid insert embodiments. The ocular preparation can also be in the form of an ointment which is compounded, for example, by mixing finely milled powdered ingredients with a small amount of petrolatum (e.g., white petrolatum) and levigating or otherwise mixing until a uniform distribution is achieved with the balance of the petrolatum being added by geometric addition until the desired dosage form is made.

The dermatan sulfate and/or O-desulfated heparin can also be formulated for intranasal delivery. See Mousa et al., "Intranasal Antiplatelet/Antithrombotic Efficacy of a Novel Platelet GPIIB/IIIA Receptor Antagonist DMP755," *Thromb. Res.* (1998) 92:115-124, which is incorporated by reference. The dermatan sulfate and/or O-desulfated heparin can also be formulated for delivery through a transdermal patch, or as a rectal suppository.

The dermatan sulfates and/or O-desulfated heparins of this invention (with or without additional actives such as heparin lyase) can also be formulated as a therapeutic composition or packaged drug product that is provided with a set of instructions for administering the composition/drug to treat a patient in need thereof. The set of instructions can be written or printed on a sheet of paper, can be on the packaging associated with the packaged drug (e.g., on the package label), can be in the form of electronic media or software (e.g., in the form of a floppy disk(s), CD ROM disk(s) or other non-volatile electronic storage media) that can be loaded, installed (directly or by downloading from a remote site such as via a LAN, WAN or the Internet), or otherwise can be read by a computer, personal digital assistant (PDA) or other electronic device, or any other suitable method for providing instructions on how to administer the composition/drug to treat the patient.

3. Pharmacological Testing a. Preparation of Test Samples

The following describe the preparation of test samples, including specific embodiments of the dermatan sulfate and O-desulfated heparin HIT antagonists of this invention (see Examples 1, 2, 3, 5, 6 and 7), for pharmacological testing:

Sample 1: Oversulfated Dermatan Sulfate (OD)

Under constant agitation, 134 g. of native dermatan sulfate (Celsus Laboratories, Cincinnati Ohio, Lot No. DI-11398) having an average molecular weight of 30,000 Daltons, an optical rotation of −54°, a sulfate/carboxylate ratio of 1.0, a heparin assay of 6 u/mg, AT-III/anti-IIa activity of 4.1 u/mg and a HCII/anti-IIa activity of approximately 7 u/mg is solubilized in 1800 ml of formamide previously dried over 4 Å molecular sieves. Then, 200 g. (32 mmol.) of trimethylamine sulfur trioxide is added to the reactor which is protected from moisture with a calcium chloride drying tube. The mixture is reacted for 24 hours at 53° C. The product of the reaction is transferred to 4 liters of 95% ethanol, and held for 30 minutes followed by the addition of 4 liters of 2% (w/v) aqueous sodium chloride solution. The pH is adjusted to neutrality and the solution sanitized, decolorized and diafiltered against purified water to a conductivity of not more than 200 μSem. The product (OD) is concentrated and lyophilized, giving 112 g for an 84% yield. The product has an AT-III/anti-IIa activity of less than 1 u/mg, HCII/anti-IIa activity of 92 u/mg; a sulfate/carboxylate ratio of 1.62, 8.6% sulfur content, Mn=21269, Mw=32064 and Mw/Mn=1.51.

Sample 2: Low Molecular Weight Dermatan Sulfate (FI) from OD

To 200 mg OD of Sample 1 dissolved in 5 ml distilled water are added 50 mg $NaIO_4$. After 3 hours oxidation at room temperature, 24 mg $NaBH_4$ is added to the reaction mixture and the reaction is allowed to proceed at room temperature. After 2 hours, the pH is adjusted to 3.2 by addition of concentrated HCl heated at 50° C. for 2 h and the pH is adjusted to 7.00 with 1N NaOH. The resulting solution is dialyzed for 6 days against 1000 MWCO membrane, and subsequently freeze-dried to afford a white powder. The overall yield is 84.7% giving a product (FI) with a HCII/anti-IIa activity of 18 u/mg; a sulfate/carboxylate ratio of 1.56; an average molecular weight of 4300 Daltons; 8.32% sulfur content, Mn=3568, Mw=5100 and Mw/Mn=1.43.

Sample 3: Low Molecular Weight Dermatan Sulfate (FD)

One hundred fifty grams of dermatan sulfate having an average molecular weight of 33,000 Daltons, an optical rotation of −54°, a heparin assay of <8 u/mg and a HCII/anti-IIa activity of less than 15 u/mg is solubilized in 1500 ml purified water. The solution is mixed with Amberlite IR-120 cation exchange resin (Rohm & Haas) for 20 minutes at pH 4.0, filtered through a 3 μm polypropylene filter and washed with 300 ml purified water. The sample is then heated to 75° C. and adjusted to 1.6% $H_2O_2$ (v/v). The material is subsequently depolymerized at 260° F. using a steam sterilizer at 23 psi for 7 minutes. The solution is then cooled to 40° C., adjusted to pH 6.5-7.0, precipitated with 2 volumes of 95% ethanol and allowed to settle overnight. The average yield of the dried product (FD) is 89% and having an average molecular weight of 3740 Daltons, an optical rotation of −35°, 5.9% sulfur content, a calculated sulfate/carboxylate ratio of 1.11, heparin assay of 2.6 u/mg and a HCII/anti-IIa activity of approximately 6 u/mg.

Sample 4: Low Molecular Weight Dermatan Sulfate (FO) from FD

Under constant agitation, 67 g. of low molecular weight dermatan sulfate (FD) of Sample 3 is solubilized in 900 ml of formamide previously dried over 4 Å molecular sieves. Then, 100 g. of trimethylamine sulfur trioxide is added to the reactor and the mixture was reacted for 24 hours at 53° C. The product of the reaction is transferred to 1 liter of 95% ethanol, and held for 30 minutes followed by the addition of 1 liter of 95% ethanol and allowed to settle for 3 hours at room temperature. The precipitate is redissolved in 500 ml purified water, adjusted to pH 6 and then again precipitated by the addition of 1 L 95% ethanol and the product dried. The product (FO) has a HCII/anti-IIa activity of 23 u/mg, an average molecular weight of 4300 Daltons, a sulfate/carboxylate ratio of approximately 1.8 and a sulfur content of approximately 9.95%.

Sample 5: Preparation of 2-O-, 3-O-Desulfated Heparin

Six hundred and fifty grams of heparin sodium are dissolved in 12 L purified water, adjusted to 1% sodium borohydride and allowed to react for 24 hours at room temperature. The solution is then adjusted to a final concentration of 0.425 M NaOH and lyophilized. The product is dissolved in purified water to 5% (w/v), precipitated with 3 volumes of 95% ethanol, extensively diafiltered to a conductivity of not more than 2.5 mS and lyophilized. The product has a USP potency of less than 3 u/mg, an anti-factor Xa activity of less than 10 u/mg, a sulfate/carboxylate ratio of 1.37, and an average molecular weight of 11,990.

b. Description of Testing and Results

Test 1: Platelet Release of Serotonin in Presence of HIT Sera (SRA)

Platelet-rich plasma is labeled with 0.1 μCi $^{14}$C-serotnin/ml. Twenty μl of HIT serum is incubated with 70 μl of platelet suspension (300,000 platelets/μl) in the presence of HIT antibody only (HIT Antibody), or HIT antibody in the presence of either increasing amounts of FI (1-5 mg/ml), or UFH (0.1 and 0.5 u/ml). The reaction is stopped by EDTA and the amount of $^{14}$C-serotonin released is determined. The results of this testing are shown in FIG. 1. As can be seen in FIG. 1, complexes of FI and platelet proteins do not stimulate platelets to release serotonin in the presence of HIT sera.

Test 2: Platelet P-Selectin Cell Surface Expression in Presence of HIT Sera

Figure 2:
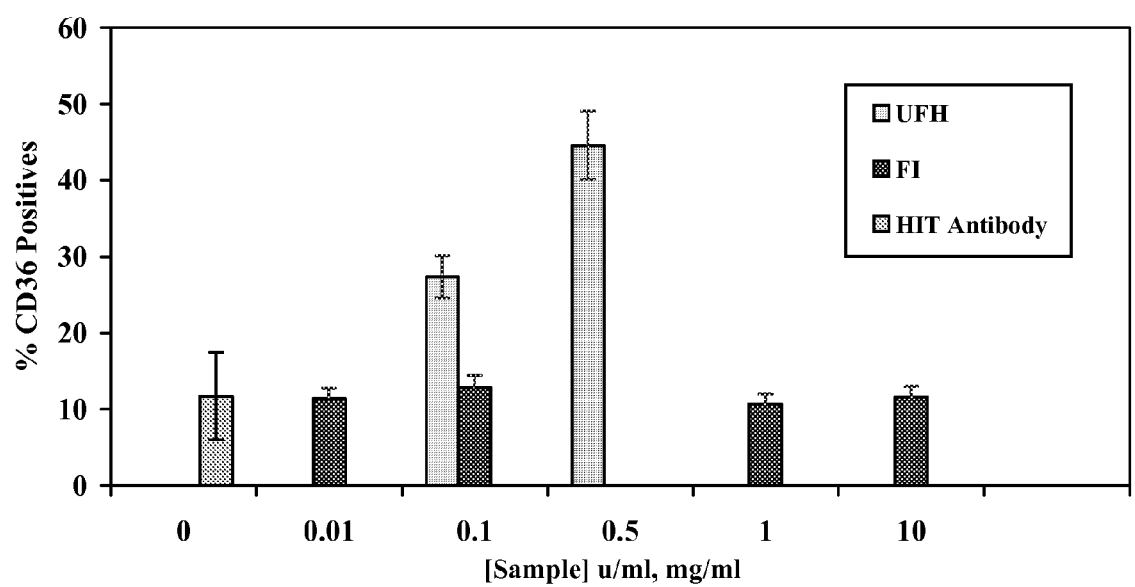
FIG. 2 is a graphical plot of testing of several test samples, at various concentrations, for cross reactivity with heparin antibodies from patients with HIT, as measured by the P-selectin expression assay.

Platelets are drawn from healthy human volunteers known not to have had exposure to drugs that interfere with platelet function. Whole blood (290 μl) is incubated with HIT serum (160 μl) in the presence of HIT antibody only (HIT Antibody), or HIT antibody either in the presence of increasing amounts of FI (0.01-10 mg/ml), or UFH (0.1 and 0.5 u/ml). P-Selectin expression is determined by flow cytometry using fluorescein isothiocyanate conjugated anti-CD61 antibody. The results of this testing are shown in FIG. 2. As can be seen in FIG. 2, complexes of FI and platelet proteins do not induce platelet P-selectin cell surface expression in the presence of HIT sera.

Test 3: Production of Procoagulant Microparticles in Presence of HIT Sera

Figure 3:
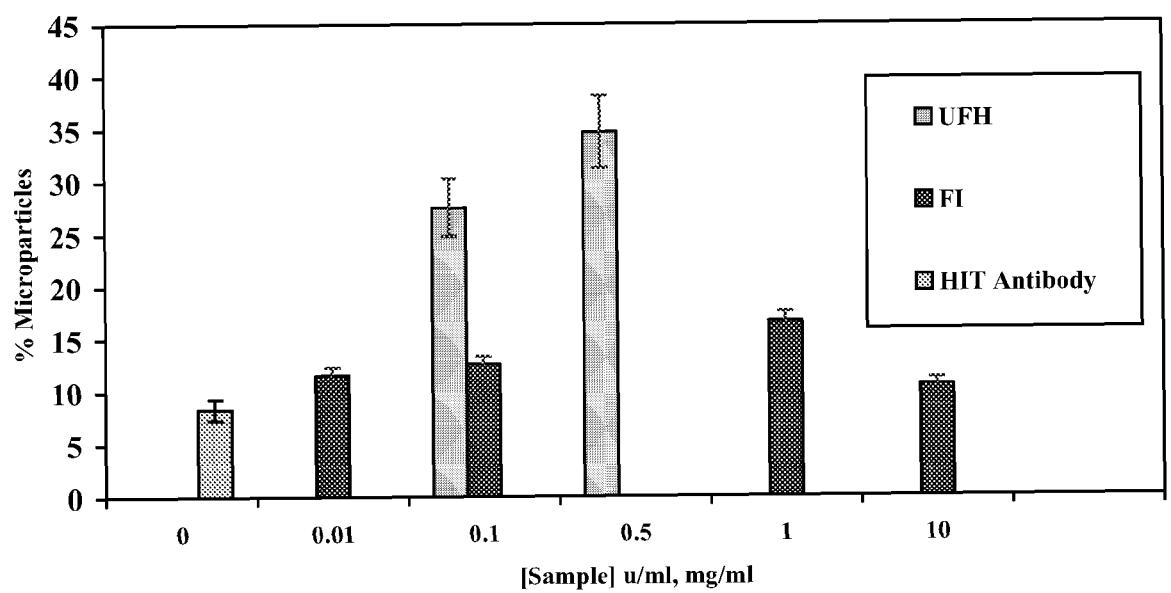
FIG. 3 is a graphical plot of testing of several test samples, at various concentrations, for cross reactivity with heparin antibodies from patients with HIT, as determined by platelet microparticle release.

Whole blood (290 μl) is incubated with HIT serum (160 μl) in the presence of HIT antibody only (HIT antibody), or HIT antibody either in the presence of increasing amounts of FI (0.01-10 mg/ml), or UFH (0.1 and 0.5 u/ml). Platelet microparticle release is determined by flow cytometry. The results of this testing are shown in FIG. 3. As can be seen in FIG. 3, complexes of FI and platelet proteins do not stimulate platelets to produce procoagulant microparticles in the presence of HIT sera.

Test 4: Antagonizing the Ability of Immune Complexes to Activate Platelets (SRA)

Figure 4:
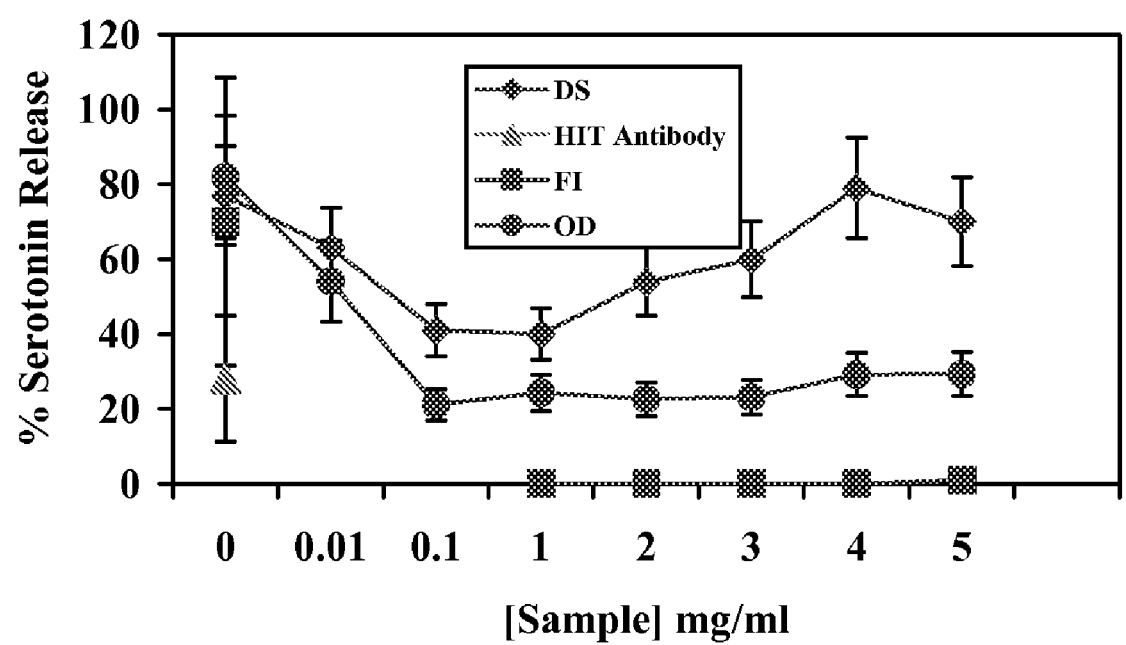
FIG. 4 is a graphical plot of the HIT antagonistic properties of several test samples at various concentrations, as measured by the SRA in the presence of UFH.

Platelet-rich plasma is labeled with 0.1 μCi $^{14}$C-serotnin/ml. Twenty μl of HIT serum (source for HIT antibody) is first incubated alone as the control (HIT Antibody) and with UFH at 0.1 U/ml, followed by the addition of increasing concentrations of DS, OD or FI (LMWDS), followed by the addition of human platelets. The amount of $^{14}$C-serotonin released in the assay is determined as described in Test 1 above. The results of this testing are shown in FIG. 4. As can be seen in FIG. 4, increasing the sulfation (OD and FI) and decreasing the molecular weight (FI) improve the ability of dermatan sulfates to antagonize the activation of platelets by preformed immune complexes comprised of heparin, platelet proteins and anti-heparin antibody.

Figure 5:
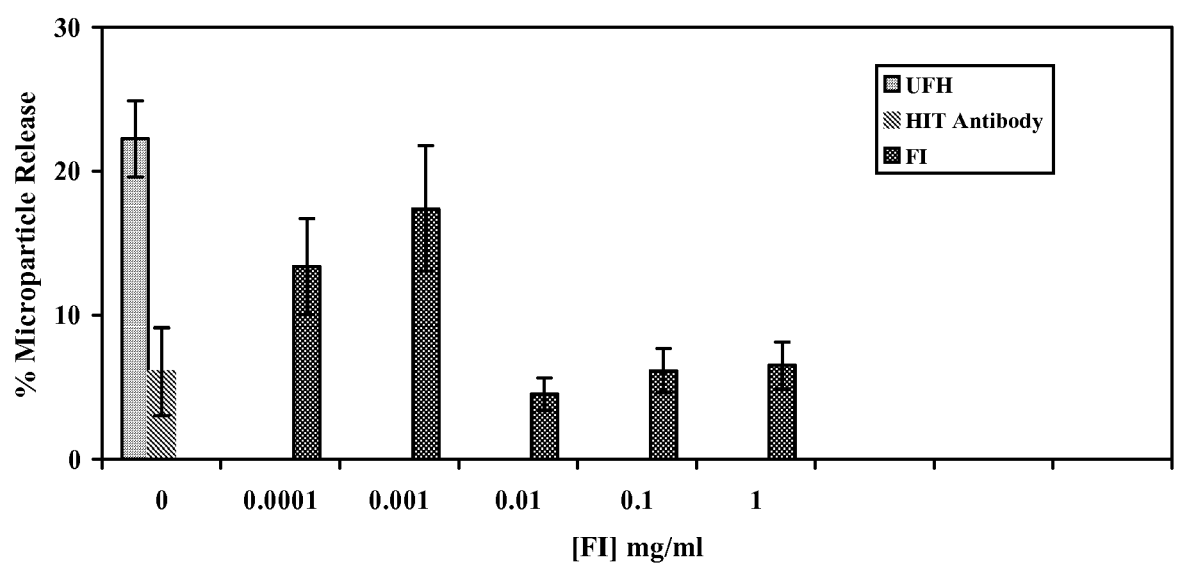
FIG. 5 is a graphical plot of the testing of several test samples at various concentrations in inhibiting heparin/heparin antibody-induced release of platelet microparticles in the presence of UFH.

Test 5: Antagonizing Heparin/Heparin Antibody-Induced Release of Platelet Microparticles Whole blood (290 μl) is incubated with HIT serum (160 μl) the absence of (HIT antibody alone) and in the presence of UFH (0.1 u/ml) and in the presence of increasing amounts of FI (0.0001-1 mg/ml). Platelet microparticle release is determined by flow cytometry similar to that described in Test 3 above. The results of this testing are shown in FIG. 5. As can be seen in FIG. 5, the addition of FI blocks the ability of preformed immune complexes comprised of heparin, platelet proteins and anti-heparin antibody to induce the release of platelet microparticles.

Test 6: Antagonizing the Ability of Immune Complexes to Activate Platelets (SRA)

Figure 6:
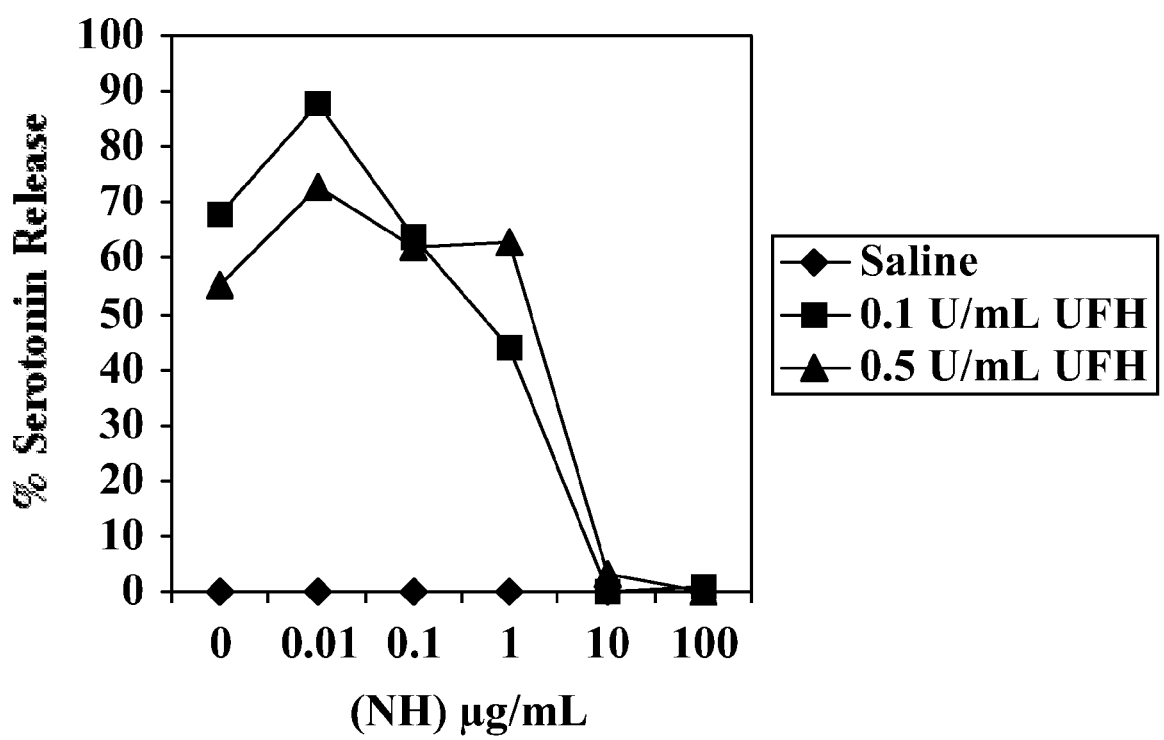
FIG. 6 is a graphical plot of the HIT agonist and antagonistic properties of an O-desulfated heparin test sample at various concentrations, as measured by the SRA in the presence of either 0.1 u/mL or 0.5 u/mL UFH.

Platelet-rich plasma is labeled with 0.1 μCi $^{14}$C-serotnin/ml. Twenty μl of HIT serum (source for HIT antibody) is first incubated in saline alone as the control (Saline) and also with UFH at either 0.1 U/ml or at 0.5 U/ml. Next increasing concentrations of selectively 2-O, 3-O desulfated heparin (Lot# NH 001603), are added to each of the test series followed by the addition of human platelets. The amount of $^{14}$C-serotonin released in the assay is determined as described in Test 1 above. The results of this testing are shown in FIG. 6. As can be seen in FIG. 6, in the absence of added UFH, the O-desulfated heparin does not cross react with HIT immune sera and platelet proteins in a manner that leads to platelet activation at O-desulfated heparin concentrations up to 100 μg/ml. Further, O-desulfated heparin causes a dose-dependent inhibition of the heparin-induced serotonin release from platelets exposed to HIT immune sera and thus, antagonizes the activation of platelets by preformed immune complexes comprised of heparin, platelet proteins and anti-heparin antibody.

Figure 7:
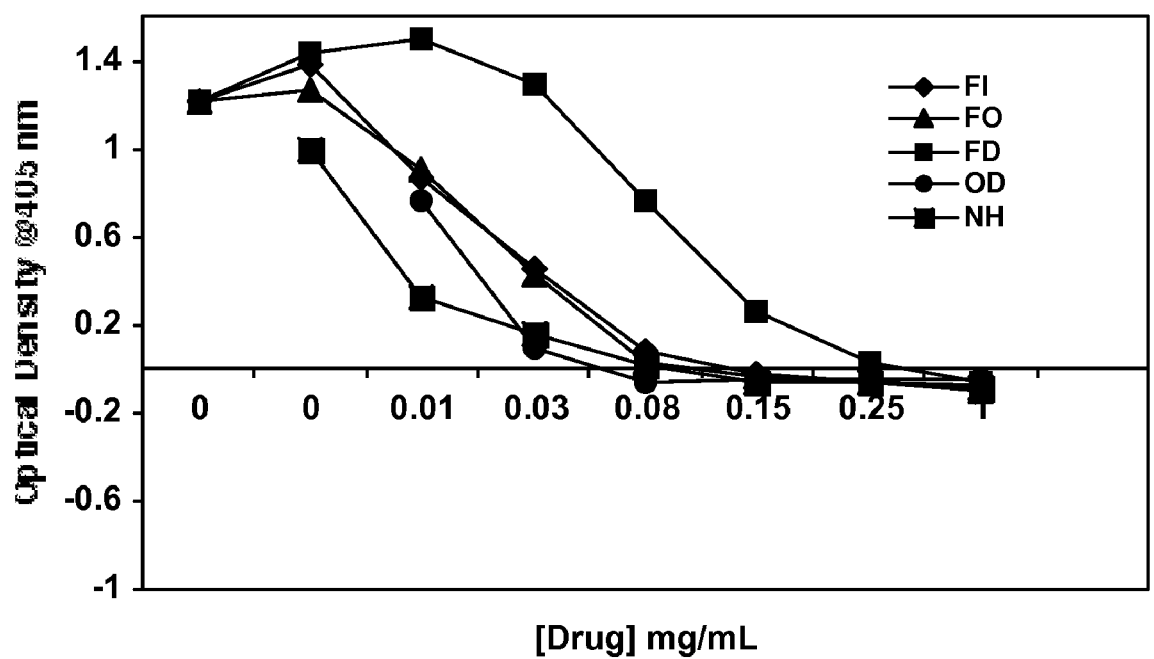
FIG. 7 is a graphical plot of the testing of several dermatan sulfate and O-desulfated heparin test samples at various concentrations in inhibiting the immunoreactivity of polyvinyl sulfonate-PF4 complexes with HIT antibodies, as detected by the ELISA assay.

Test 7: Inhibiting Immunoreactivity of HIT Antibodies with Polyvinyl Sulfonate-PF4 Antigenic Complexes as Detected by ELISA Assay Preformed antigenic complexes comprised of polyvinylsulfonate (PVS) and PF4 bound to microtiter wells are incubated with increasing concentrations of FD, FI, FO, OD or NH test samples, are washed to remove the residual sample, and are then incubated with human HIT immune serum (or nonimmune serum as control). The amount of immune complex formation is then detected with alkaline phosphatase conjugated to goat anti-human IgG (affinity-purified antibody) by reaction with p-nitrophenyl phosphate as the enzyme substrate and then determined spectrophotometrically at 405 nm. Values are corrected for nonimmune serum controls. The results graphically plotted in FIG. 7 show FI, FO, OD and NH disrupt neoepitope expression of PVS-PF4 complexes, and their subsequent immunoreactivity with HIT antibodies, better than FD.

All documents, patents, journal articles and other materials cited in the present application are hereby incorporated by reference.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed is:

1. A method for treating and/or inhibiting heparinoid-induced autoimmune responses, which comprises the steps of:

administering to a patient or a medical device an amount of a dermatan sulfate which is therapeutically effective to treat and/or inhibit a heparinoid-induced autoimmune response in the absence of a platelet glycoprotein IIb/IIIa receptor antagonist, the dermatan sulfate comprising repeating disulfated and/or trisulfated disaccharide units of L-iduronic acid and N-acetyl-D-galactosamine and having the following properties: (1) a molecular weight in the range of from about 1200 to about 35,000 Daltons; (2) a sulfur content in the range from about 6 to about 11%; (3) a sulfate/carboxylate ratio (S/C) in the range of from about 1.2 to about 2.0; (4) a combined disulfated and trisulfated disaccharide content in the range of from about 20 to 100%; (5) less than about 20% platelet activation activity in the presence of HIT immune sera or anti-heparin/PF4 antibody; and (6) an ability to inhibit the activation of human platelets caused by HIT reactive sulfated glycosaminoglycans in the presence of either HIT immune sera or anti-heparin/PF4 antibody; and administering to the patient or the medical device an amount of a heparin lyase which is effective to degrade heparin.

2. The method of claim 1 wherein the dermatan sulfate has: (7) an $IC_{50}$ of less than about 250 μg/ml in the presence of added Heparin Sodium USP at 0.1 u/ml; and (8) a heparin cofactor II activity of at least about 15 u/mg.

3. The method of claim 2 wherein the dermatan sulfate has: (2) a sulfur content of from about 8 to about 11%; (3) a sulfate/carboxyl ratio of from about 1.45 to about 2.0; (4) a combined disulfated and trisulfated disaccharide content of from about 45 to 100%; (7) an $IC_{50}$ of less than about 150 μg/ml; and (8) a heparin cofactor II activity of from about 60 to about 130 u/mg.

4. The method of claim 1 wherein the dermatan sulfate comprises the 4,6-disulfated disaccharide species, the 2,4-disulfated disaccharide species, and/or the 2,4,6-trisulfated disaccharide species.

5. The method of claim 1 wherein the dermatan sulfate has a mean molecular weight of from about 2000 to about 10,000 Daltons.

6. The method of claim 5 wherein the dermatan sulfate has a ratio of the weight average mean molecular weight to the number average mean molecular weight of from about 1.2 to about 1.8.

7. The method of claim 5 wherein the dermatan sulfate has a mean molecular weight of from about 3500 to about 8500 Daltons; and a ratio of the weight average molecular weight to the number average molecular weight of from about 1.3 to about 1.6.

8. The method of claim 1 wherein the heparinoid-induced autoimmune response that is treated and/or inhibited by the administration of the dermatan sulfate is heparin-induced thrombocytopenia.

9. The method of claim 1 wherein the heparinoid-induced autoimmune response that is treated and/or inhibited by the administration of the dermatan sulfate is the formation and/or presence of heparin-induced immune complexes.

10. The method of claim 1 wherein the heparinoid-induced autoimmune response that is treated and/or inhibited by the administration of the dermatan sulfate are activated platelets, endothelium, and/or monocytes.

11. The method of claim 1 wherein the dermatan sulfate is administered to treat and/or inhibit the impairment of a medical device that is coated with a heparinoid, or interacts with or is exposed to blood.

12. The method of claim 11 wherein the medical device is provided with a source of the dermatan sulfate that is delivered to the medical device.

13. The method of claim 12 wherein the medical device is coated with the dermatan sulfate.

14. The method of claim 13 wherein the medical device is a stent, a catheter, a vascular graft, a heart-lung bypass machine, a hemodialysis unit, a drug delivery unit, an oxygenator, a filter, a membrane, or medical device circuitry.

15. The method of claim 1 wherein the heparinoid-induced autoimmune response that is treated and/or inhibited by the administration of the dermatan sulfate is a vascular access obstruction.

16. The method of claim 1 wherein the dermatan sulfate is administered to a patient.

17. The method of claim 16 wherein the patient that the dermatan sulfate is administered to is a human.

18. The method of claim 1 wherein the dermatan sulfate and heparin lyase are administered as separate doses.

19. The method of claim 1 wherein the dermatan sulfate and heparin lyase are administered as a combined dose.

* * * * *